(12) United States Patent
Port

(10) Patent No.: US 8,114,863 B2
(45) Date of Patent: Feb. 14, 2012

(54) COMPOUNDS COMPRISING SHORT AMINOALCOHOL CHAINS AND METAL COMPLEXES FOR MEDICAL IMAGING

(75) Inventor: Marc Port, Deuil la Barre (FR)

(73) Assignee: Guerbet, Villepinte (FR)

( * ) Notice: Subject to any disclaimer, the term of this patent is extended or adjusted under 35 U.S.C. 154(b) by 711 days.

(21) Appl. No.: 12/083,092

(22) PCT Filed: Oct. 9, 2006

(86) PCT No.: PCT/EP2006/067214
§ 371 (c)(1),
(2), (4) Date: Jul. 18, 2008

(87) PCT Pub. No.: WO2007/042506
PCT Pub. Date: Apr. 19, 2007

(65) Prior Publication Data
US 2009/0169479 A1 Jul. 2, 2009

Related U.S. Application Data

(60) Provisional application No. 60/734,756, filed on Nov. 9, 2005.

(30) Foreign Application Priority Data

Oct. 7, 2005 (FR) .................................... 05 10289

(51) Int. Cl.
*A61K 31/33* (2006.01)
*C07D 257/02* (2006.01)
(52) U.S. Cl. ........................................ 514/183; 540/474
(58) Field of Classification Search ........................ None
See application file for complete search history.

(56) References Cited

U.S. PATENT DOCUMENTS 3,135,748 A 6/1964 Sheehan
5,712,389 A * 1/1998 Meyer et al. .................. 540/474
6,071,490 A 6/2000 Griffiths et al.
(Continued)

FOREIGN PATENT DOCUMENTS
EP 0 438 206 A1 7/1991
(Continued)

OTHER PUBLICATIONS

Fulton et al. Chemical Communications, 2006, 1064-1066.*

*Primary Examiner* — Noble Jarrell
(74) *Attorney, Agent, or Firm* — Birch, Stewart, Kolasch & Birch, LLP

(57) ABSTRACT

The present invention relates to a compound of formula (II) chosen from (IIa) and (IIb) or of formula (VI) chosen from (VIa) and (VIb) of following general formulae:

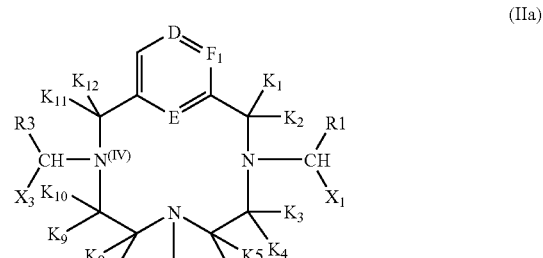

(IIa)

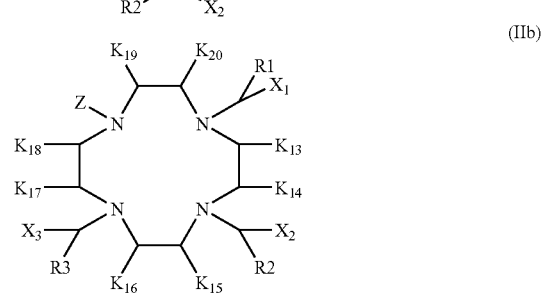

(IIb)

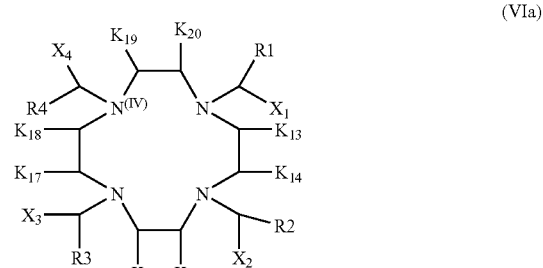

(VIa)

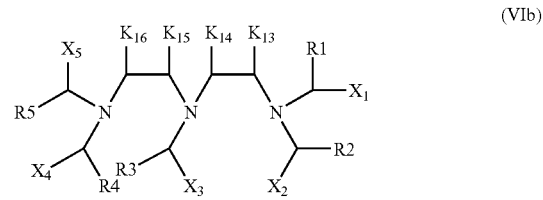

(VIb)

in which:

$X_1$, $X_2$, $X_3$, $X_4$ and $X_5$ represent, independently of one another, L-Y in which L represents a $C_1$-$C_3$ alkyl group, preferably $(CH_2)_n$ with n=1 to 3, Y represents —$CONH_2$, —CO—NR7R8 or —NR8-CO—R8, or an isomer, an enantiomer or a diastereoisomer of these or their mixtures or a pharmaceutically acceptable salt of the compounds of formulae (VIa) and (VIb).

It also relates to a complex of these compounds with a paramagnetic metal or a radionuclide and their use in diagnostic methods.

16 Claims, No Drawings

U.S. PATENT DOCUMENTS

| | | |
|---|---|---|
| 6,264,914 B1 | 7/2001 | Klaveness et al. |
| 6,440,956 B1 | 8/2002 | Port |
| 6,537,520 B1 | 3/2003 | Rajopadhye et al. |
| 6,827,927 B1 | 12/2004 | Rousseaux et al. |
| 2004/0210041 A1 | 10/2004 | Arbogast et al. |
| 2007/0258905 A1 | 11/2007 | Aime et al. |

FOREIGN PATENT DOCUMENTS

| | | |
|---|---|---|
| EP | 0 661 279 A1 | 7/1995 |
| WO | WO-93/11800 A1 | 6/1993 |
| WO | WO-00/71526 A1 | 11/2000 |
| WO | WO-01/09188 A1 | 2/2001 |
| WO | WO-01/52900 A2 | 7/2001 |
| WO | WO-03/008390 A1 | 1/2003 |
| WO | WO-03/074523 A2 | 9/2003 |
| WO | WO-2004/112839 A2 | 12/2004 |
| WO | WO-2005/001415 A2 | 1/2005 |
| WO | WO-2005/009393 A2 | 3/2005 |
| WO | WO-2005/042033 A1 | 5/2005 |
| WO | WO-2005/049005 A1 | 6/2005 |
| WO | WO-2005/049095 A2 | 6/2005 |
| WO | WO-2005/062828 A2 | 7/2005 |
| WO | WO-2006/002873 A2 | 1/2006 |

\* cited by examiner

COMPOUNDS COMPRISING SHORT AMINOALCOHOL CHAINS AND METAL COMPLEXES FOR MEDICAL IMAGING

The invention relates to novel compounds of use for diagnostic medical imaging and to pharmaceutical compositions comprising these compounds. These compounds are used in particular as contrast agents for MRI.

The administration of contrast products to patients contributes to improving the resolution of the images obtained and the accuracy of the diagnosis. A person skilled in the art thus knows, for MRI (magnetic resonance imaging), a large number of contrast products, referred to as non-specific contrast products, based on linear or macrocyclic gadolinium chelates, for example the compounds DTPA, DTPA BMA, DTPA BOPTA, DO3A, DOTA. Contrast products, comprising paramagnetic or superparamagnetic metals, modify the relaxation time of the protons and the increase in the relaxivity obtained makes it possible to obtain a stronger signal and a higher spatial resolution. The gadolinium chelates used in human clinical treatment, such as Magnevist® (DTPA), Dotarem® (DOTA) or Omniscan® (DTPA BMA), are of low molecular weight, have molar relaxivities r1 per Gd of the order of 3 to 4 $mM^{-1}s^{-1}$ at the usual magnetic fields of 0.5 to 1.5 tesla. These compounds are properly referred to as non-specific compounds, that is to say having a broad spectrum of diagnostic indications, even if they may be more or less suitable for certain diagnostic indications, in comparison with compounds designed specifically for the targeting of highly specific indications. For example, the prior art discloses a great many compounds comprising a signal part (such as a DOTA or DTPA derivative) and a targeting part (for example peptide) intended to specifically recognize one or more biological molecules generally overexpressed in certain pathologies, such as cancers, inflammatory diseases or cardiovascular diseases.

The need remains to find novel compounds, in particular non-specific compounds, the synthesis of which is not too complex and which have a significantly better relaxivity than that of the non-specific chelates already known, in order to increase the efficiency in diagnostic imaging.

Among known chelates, bicyclopolyazamacrocyclocarboxylic acid chelates of formula (I) have been disclosed in particular in the document EP 438 206:

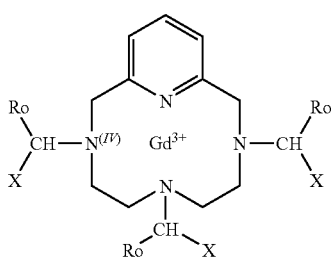

(I)

in which X represents a carboxylate or phosphate group and Ro represents an alkyl or phenyl group, or one of the Ro symbols is a group forming a bond with a biological molecule. Among these compounds, the following compound, denoted PCTA in the remainder of the description, is known to a person skilled in the art (Inorganic Chemistry, 36(14), 2992-3000 (1997), and Magn. Reson. Chem., 36, S200-208 (1998)).

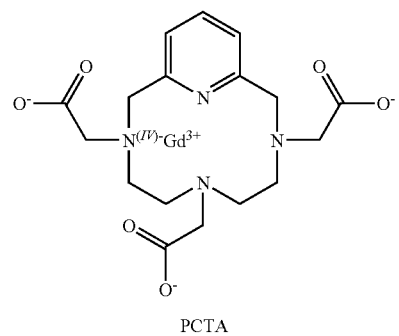

PCTA

The known compounds having the backbone of formula (I) of PCTA type have a relaxivity of the order of 4 to 6 $mM^{-1}s^{-1}Gd^{-1}$.

It should be remembered that the compounds of formula (I) are advantageous as they make possible the exchanges of two water molecules per chelate in order to complete the coordination sphere of the gadolinium (9 possible interactions) present in the chelate. This is because the PCTA backbone contributes 7 potential interactions (4 nitrogen atoms+3 acid functional groups), which leaves an interaction between the gadolinium and 2 water molecules, denoted q=2 (that is to say, 9-7).

More specifically, the document WO 93/11800 discloses compounds of formula (I) with Ro groups chosen from H, OH or $C_1$-$C_3$ alkyl. The document U.S. Pat. No. 5,403,572 discloses compounds in which the Ro groups can be alcohols; the synthesis of these compounds involves the synthesis of the alcohol chain and then, by an alkylation reaction, the coupling of this chain with the nitrogen atoms of the macrocycle.

Such compounds, the Ro groups of which are alkyls or alcohols, are liable to exhibit fairly variable and rather low relaxivities, as will be described later.

Moreover, the document U.S. Pat. No. 6,450,956 discloses compounds with Ro=-$CH_2$—$CH_2$—CO—NH—Y, in which Y necessarily represents a heavy aminoalcohol chain, with examples of chains with a molecular weight of approximately 500 to 1500. These compounds of molecular weight in the order of 3000 have a very high relaxivity, of the order of 20 to 30 $mM^{-1}s^{-1}Gd^{-1}$, but present the problem of an expensive synthesis industrially and of an excessively high viscosity, it not being possible for their concentration during their administration to be very high. Furthermore, these compounds can exhibit highly specific properties in the vascular compartment, such as slow diffusion agent behaviour (LDA), which are not necessarily desired for a non-specific compound or compound of low specificity. In particular, these compounds can diffuse into the central nervous system.

An important problem to be solved is thus that of succeeding in obtaining novel compounds exhibiting both a simplified chemical synthesis and a markedly improved relaxivity in comparison with the non-specific compounds already described or available commercially.

Another problem is that of obtaining compounds having an efficiency in imaging (relaxivity) which is not detrimentally affected when used at high magnetic field, in particular above 3 tesla. This is because medical imaging devices are evolving in the direction of an increase in the field. It should be remembered that the relaxivity of numerous known compounds comprising a DOTA, DTPA or DO3A backbone decreases markedly at high field.

Surprisingly, the Applicant has succeeded in obtaining very efficient products by grafting branches, no longer heavy and complex but, on the contrary, short, to the chains in the α position with respect to the chelating carboxyl functional groups. The results are particularly advantageous using aminoalcohol chains, this being the situation especially in the case of the compounds exhibiting a value of q=2 (in particular, chelates of PCTA and DO3A type), and thus form compounds referred to as compounds (II) in the remainder of the description.

The Applicant has thus obtained compounds which, when they are complexed with a metal, have a relaxivity (efficiency in imaging) and a mass efficiency (industrial cost price) which are very markedly improved, with r1 values of the order of 9 to 15 mM$^{-1}$s$^{-1}$Gd$^{-1}$, that is to say multiplied by a factor of 2 to 3 with respect to previous derivatives, in particular PCTA, DO3A, DOTA or DTPA.

These compounds (II), when they do not comprise a biological targeting part, exhibit several functional characteristics which are particularly outstanding once combined:

- non-ionicity: this makes it possible to greatly restrict the osmolality of the product to be injected and thus the dose of product injected, which is an advantageous criteria for contrast products in order to improve the comfort of the patients (the osmolality being closer to the plasma osmolality), and to reduce the cost of the injection.
- high hydrophilicity: this makes possible appropriate solubility and non toxicity of the product.
- high relaxivity (high intensity of the signal): the relaxivity is high and is not detrimentally affected (unquenched) by the hydroxyl groups of the structure.
- low industrial cost price (in particular high mass efficiency): the compounds notably compounds II allow to achieve a high relaxivity of about 12 mM$^{-1}$s$^{-1}$Gd$^{-1}$ with a molecular weight of only about 800 to 1000.
- low molecular weight, making it possible to obtain a non-specific compound biodistribution: for example, undesired behaviour of blood pool agent type, which corresponds to selective diffusion into the vascular compartment, in particular, is avoided.

It was not at all obvious to anticipate the highly satisfactory physicochemical behaviour of the carboxamide functional group with respect to the gadolinium in this combination invention, nor that the shortening of the aminoalcohol chains would make it possible to retain a very good relaxivity, in contrast to the other chelates of the prior art comprising a short chain.

Furthermore, the Applicant has found, unexpectedly, that the relaxivity is stable with the magnetic field for compounds (II) complexed with a metal, which is highly advantageous in comparison with previous compounds, in particular of the document U.S. Pat. No. 6,440,956.

Thus, the invention therefore relates, according to a first aspect, to compounds (II) of formulae (IIa) and (IIb):

(IIa)

and (IIb)

in which:

R1, R2 and R3 represent, independently of one another, —COOH, —P(O)(OH)$_2$ or —R$_6$—P(O)—OH in which R$_6$ represents an H atom or a C$_1$-C$_3$ alkyl group, preferably COOH;

X$_1$, X$_2$ and X$_3$ represent, independently of one another, L-Y in which

L represents a C$_1$-C$_3$ alkyl group, preferably (CH$_2$) with n=1 to 3,

Y represents —CONH$_2$, —CO—NR7R8 or —NR7-CO—R8, in which R7 represents H or a C$_1$-C$_6$ alkyl group or a C$_1$-C$_6$ hydroxyalkyl group, in particular a C$_2$-C$_4$ group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH, with m=1 to 3, p=1 to 4 and m+p=2 to 5, or —C—(CH$_2$OH)$_3$, and R8 represents a C$_1$-C$_6$ alkyl or C$_1$-C$_6$ hydroxyalkyl group, in particular a C$_2$-C$_4$ group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH, with m=1 to 3, p=1 to 4 and m+p=2 to 5, or —C—(CH$_2$OH)$_3$, provided that at least R7 or R8 represents a C$_1$-C$_6$ hydroxyalkyl group;

D represents CH or N;
E represents CH or N;
F$_1$ represents CH or N;
Z represents H, or aryl-alkyl group, C$_1$-C$_3$ alkyl group or a C$_1$-C$_6$ hydroxyalkyl group in particular CH$_3$, CH$_2$-Aryl K$_1$ to K$_{20}$ each independently represent H, —(CH$_2$)—CH$_3$ or —(CH$_2$)$_i$—OH, in which j=0 to 3 and i=1 to 3, advantageously H, or K$_3$ or K$_4$ with K$_5$ or K$_6$, and/or K$_7$ or K$_8$ with K$_9$ or K$_{10}$, or K$_{13}$ with K$_{14}$ and/or K$_{15}$ with K$_{16}$ and/or K$_{17}$ with K$_{18}$ and/or K$_{19}$ with K$_{20}$ form a ring having 3 to 6 carbon atoms;

or an isomer, an enantiomer or a diastereoisomer of these or their mixtures.

The invention thus covers the isomers, in particular RRS, RSR, RSS isomers, of the compounds (II).

It should be remembered that "C$_1$-C$_n$" is understood to mean any group chosen from C$_1$, C$_2$, C$_3$, . . . C$_n$.

Within the meaning of the present invention, the term "alkyl" (or alkylene) is understood to mean any straight or branched and unsubstituted chain of carbon atoms (preferably 1 to 5).

Within the meaning of the present invention, the term "hydroxyalkyl group" is understood to mean any alkyl chain as defined above comprising one or more hydroxyl groups.

The term "aryl" as used in the present invention refers to a monocyclic or bicyclic carbocyclic ring system containing 5 to 8 carbon atoms and having one or more aromatic rings including, but not limited to, phenyl, naphtyl, tetrahydronaphtyl, indanyl and the like, advantageously phenyl.

Preference is particularly given to the compounds (II) in which the three Y chains each have a molecular weight of less than 200, advantageously between 50 and 100, and in particular the compounds in which the Y chains each comprise 1 to 5 OH groups. The invention also covers the compounds (II) in which m+p>5, that is to say resulting from each of the possible combinations between m=1, 2, 3 and p=1, 2, 3, 4.

According to advantageous implementations, the invention relates to compounds of formula (IIa) in which E represents an N atom and D and $F_1$ represent CH.

The data, in particular for relaxivity and solubility, are also advantageous for the compounds possessing a DOTA or DTPA backbone or other chelates exhibiting a value q=1. The invention thus relates, according to another aspect, by applying the inventive concept of the grafting of a short aminoalcohol chain, to compounds (VI) of formula (VIa) or (VIb):

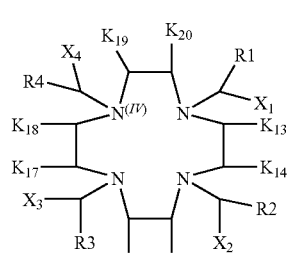
(VIa)

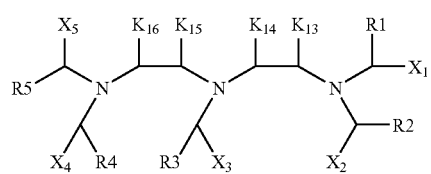
(VIb)

in which:
R1, R2, R3, R4 and R5 represent, independently of one another, —COOH, —P(O)(OH)$_2$ or —R$_6$—P(O)—OH in which R$_6$ represents an H atom or a $C_1$-$C_3$ alkyl group, preferably COOH;
$X_1$, $X_2$, $X_3$, $X_4$ and $X_5$ represent, independently of one another, L-Y in which
L represents a $C_1$-$C_3$ alkyl group, preferably (CH$_2$)$_n$ with n=1 to 3,
Y represents —CONH$_2$, —CO—NR7R8 or —NR7-CO—R8, in which R7 represents H or a $C_1$-$C_6$ alkyl group or a $C_1$-$C_6$ hydroxyalkyl group, in particular a $C_2$-$C_4$ group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH, with m=1 to 3, p=1 to 4 and m+p=2 to 5, or —C—(CH$_2$OH)$_3$, and R8 represents a $C_1$-$C_6$ alkyl or $C_1$-$C_6$ hydroxyalkyl group, in particular a $C_2$-$C_4$ group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH, with m=1 to 3, p=1 to 4 and m+p=2 to 5, or —C—(CH$_2$OH)$_3$, provided that at least R7 or R8 represents a $C_1$-$C_6$ hydroxyalkyl group;
$K_{13}$ to $K_{20}$ each independently represent H, —(CH$_2$)—CH$_3$ or —(CH$_2$)$_i$—OH, in which j=0 to 3 and i=1 to 3, advantageously H, or $K_{13}$ with $K_{14}$ and/or $K_{15}$ with $K_{16}$ and/or $K_{17}$ with $K_{18}$ and/or $K_{19}$ with $K_{20}$ form a ring having 3 to 6 carbon atoms; or an isomer, an enantiomer or a diastereoisomer of these or their mixtures or a pharmaceutically acceptable salt of these.

The invention thus covers the isomers, in particular RRRR, RSRR, RRSS, RSRS isomers, of the compounds (VIa).

The invention thus also relates to the pharmaceutically acceptable salts of the compounds of formulae (VIa) and (VIb) with inorganic or organic acids or bases, in particular the hydrochlorides of the amino groups and the sodium, potassium and N-methylglucamine salts of the carboxylic acid groups present on the chelates.

The term "salt" is defined, for example, in *CRC Handbook of Chemistry and Physics, 65th Edition*, CRC Press, Boca Raton, Fla., 1984. The term "pharmaceutically acceptable salt" refers to derivatives of the compounds according to the invention modified by forming acid or basic salts, for example inorganic or organic salts, acid salts of basic residues, such as amines, alkaline salts of acid residues, such as carboxylic acids (examples of salts: hydrochloric, hydrobromic, sulphuric, sulphamic, acetic, propionic, succinic, stearic, lactic, malic, tartaric, citric, glutamic), meglumine or lysine salts, in particular. Use may also be made of calcium and zinc salts, in particular.

Preference will be given to the compounds (VI) in which each Y chain has a molecular weight of less than 120, preferably between 20 and 100, and which have a relaxivity in water of at least 7 mM$^{-1}$s$^{-1}$Gd$^{-1}$.

The compounds (VIa) and (VIb) constitute advantageous improvements to U.S. Pat. No. 5,712,389, which covers DOTA and DTPA derivatives carrying heavy aminoalcohol chains with a molecular weight of greater than 200. Overall, the invention relates in particular to compounds chosen from:

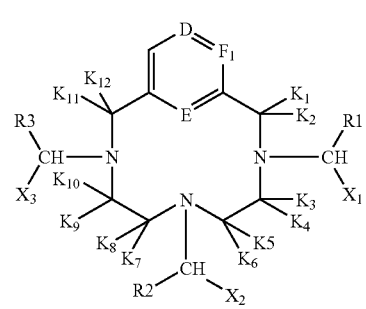
(IIa)

(IIb)

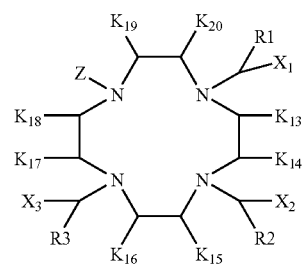
(VIa)

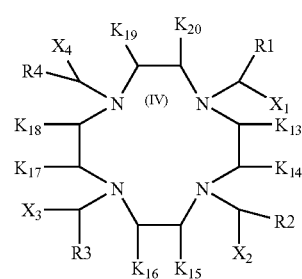
(VIb)

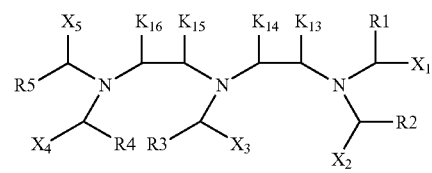

in which:

R1, R2, R3, R4 and R5 represent, independently of one another, —COOH, —P(O)(OH)$_2$ or —R$_6$—P(O)—OH in which R$_6$ represents an H atom or a C$_1$-C$_3$ alkyl group, preferably COOH;

X$_1$, X$_2$, X$_3$, X$_4$ and X$_5$ represent, independently of one another, L-Y in which L represents a C$_1$-C$_3$ alkyl group, preferably (CH$_2$)$_n$ with n=1 to 3, Y represents —CONH$_2$, —CO—NR7R8 or —NR7-CO—R8, in which R7 represents H or a C$_1$-C$_6$ alkyl group or a C$_1$-C$_6$ hydroxyalkyl group, in particular a C$_2$-C$_4$ group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH, with m=1 to 3, p=1 to 4 and m+p=2 to 5, or —C—(CH$_2$OH)$_3$, and R8 represents a C$_1$-C$_6$ alkyl or C$_1$-C$_6$ hydroxyalkyl group, in particular a C$_2$-C$_4$ group, advantageously —CH$_2$—CH$_2$OH, —CHOH—CH$_2$OH, —CH—(CH$_2$OH)$_2$, —(CH$_2$)$_m$—(CHOH)$_p$—CH$_2$OH, with m=1 to 3, p=1 to 4 and m+p=2 to 5, or —C—(CH$_2$OH)$_3$, provided that at least R7 or R8 represents a C$_1$-C$_6$ hydroxyalkyl group;

D represents CH or N;

E represents CH or N;

F$_1$ represents CH or N;

Z represents H, or aryl-alkyl group, C$_1$-C$_3$ alkyl group or a C$_1$-C$_6$ hydroxyalkyl group in particular CH$_3$, CH$_2$-Aryl K$_1$ to K$_{20}$ each independently represent H, —(CH$_2$)$_j$—CH$_3$ or —(CH$_2$)$_i$—OH, in which j=0 to 3 and i=1 to 3, advantageously H, or K$_3$ or K$_4$ with K$_5$ or K$_6$, and/or K$_7$ or K$_8$ with K$_9$ or K$_{10}$, or K$_{13}$ with K$_{14}$ and/or K$_{15}$ with K$_{16}$ and/or K$_{17}$ with K$_{18}$ and/or K$_{19}$ with K$_{20}$ form a ring having 3 to 6 carbon atoms;

or an isomer, an enantiomer or a diastereoisomer of these or their mixtures or a pharmaceutically acceptable salt of the compounds of formulae (VIa) and (VIb).

According to advantageous implementations, the invention relates to compounds of formula (II) or (VI) in which X1 to X5 independently represent —(CH$_2$)$_n$—CO—NR7R8 or —(CH$_2$)$_n$—NR7-CO—R8, in which n is between 1 and 3, R7 represents H or a methyl group and R8 represents a C$_1$-C$_6$, advantageously C$_2$-C$_3$, hydroxyalkyl group, preferably —CH$_2$—CH$_2$OH, —CHOH—CH$_2$OH, —CH—(CH$_2$OH)$_2$, —CH$_2$—(CHOH)$_p$—CH$_2$OH, with p=1 to 4, or —C—(CH$_2$OH)$_3$.

Advantageously, X1 to X5 independently represent —(CH$_2$)$_n$—CONR7R8, in which n is between 1 and 3, R7 represents H or a methyl group and R8 represents a C$_1$-C$_4$ hydroxyalkyl group, preferably —CH$_2$—CH$_2$OH, —CHOH—CH$_2$OH, —CH—(CH$_2$OH)$_2$, —CH$_2$—(CHOH)$_p$—CH$_2$OH with p=1 or 2, or —C—(CH$_2$OH)$_3$.

Advantageously, X1 to X5 independently represent —(CH$_2$)$_n$—CONR7R8, in which n is between 1 and 3, R7 represents H and R8 represents —CH$_2$—CH$_2$OH, —CHOH—CH$_2$OH, —CH—(CH$_2$OH)$_2$, —CH$_2$—(CHOH)$_p$—CH$_2$OH, with p=1 to 4, or —C—(CH$_2$OH)$_3$.

More probably, the Applicant has taken an interest in compounds (II) and (VI) exhibiting the characteristics d) to f) below to be studied in terms of functional equivalence (relaxivity, physical chemistry, biodistribution) in comparison with the compounds (II) and (VI) described above:

d) Compound of following formula (IIc)

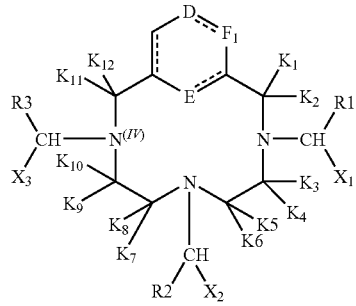

in which E is chosen from N, S, O, =C; F$_1$ is chosen from (—CHR9-)$_n$ or (=CR9-)$_n$ with R9 having the meaning indicated in the document U.S. Pat. No. 5,403,572, column 63; D is chosen from N, O, C=O, —ND1 with D1 being chosen from H, a C$_1$-C$_3$ alkyl, —CH-D2, =C-D2-, with D2 being chosen from: H, C$_1$-C$_3$ alkyl (optionally substituted by one or more hydroxyl groups), —O-D3 (with D3 a C$_1$-C$_3$ alkyl optionally substituted by hydroxyl groups or D3 being —(CH$_2$)$_m$—CO—N-D4, D4 being chosen analogously to the document U.S. Pat. No. 5,403,572);

e) L is an alkyl chain (linear or branched hydrocarbon chain comprising up to 6 carbons which is optionally substituted by hydroxyl or phenyl groups) or L is an alkylene chain of 1 to 6 carbon atoms which is optionally interrupted by one or more oxygen atoms, one or more hydroxymethylene (CHOH) groups, imino groups, one or more double or triple bonds;

f) Y is an A-B-R2 chain in which A-B is a functional group other than a carboxamide functional group CONH or than a carbonylamino functional group NHCO; in particular, A is functional group chosen from: —NCS, —NH—NH$_2$, —CHO, alkylpyrocarbonyl (—CO—O—CO-alkyl), acylazidyl (—CO—N$_3$), iminocarbonate (—O—C(NH)—NH$_2$), vinylsulphuryl (—S—CH=CH$_2$), pyridyldisulphuryl (—S—S-Py), haloacetyl, maleimidyl, dichlorotriazinyl or halogen;

with, for example, the A-B group forming a covalent bond of —COO—, —OCO—, —NH—CS—NH—, —CH$_2$—S—, —NH—NH—CO—, —CO—NH—NH—, —CH$_2$—NH—, —NH—CH$_2$—, —NH—CS—N—, —CO—CH$_2$—S—, —NH—CO—CH$_2$—S—, —N—CO—CH$_2$—CH$_2$—S—, —CH=NH—NH—, —NH—NH=CH—, —CH=N—O— or —O—N=CH— type;

The Applicant has also studied compounds in which Y represents a carbamoyl group CONR'2R'3 in which R'2 and R'3 are each independently a chain other than a hydroxyalkyl and in particular a group chosen from alkyl (linear or substituted), alkoxy (that is to say, alkyl-O—), alkoxycarbonyl (that is to say, alkoxy-C=O), cycloalkyl, alkoxyalkyl, aryl (in particular phenyl, pyridyl, furyl) or aralkyl (that is to say, an aryl group bonded to an alkyl group) groups.

According to another aspect, the invention relates to the multimers (advantageously the dimers or trimers) of the compounds of formulae (II) and (VI) as defined above. To produce such multimers, the compounds of formula (II) or (VI) are coupled together, advantageously via a bonding group. In particular, these bonding groups can be bonded to the compound of formula (IIa) at D. Various bonding groups can be used. The Applicant has studied in particular compounds of formula (IIa) in which D represents a —CH-G group with G having the meaning indicated in the document U.S. Pat. No. 5,403,572. In particular, G represents at least one second macrocycle of formula (II) connected via a bonding group to the first macrocycle. Bonding groups which can be used are given in columns 12 to 14 of U.S. Pat. No. 5,403,572. The Applicant has also in particular studied compounds comprising a bonding group capable of being connected to more than two macrocycles and in particular to three macrocycles (II), such as a bonding group comprising the group:

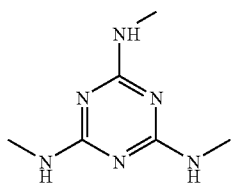

According to another aspect, the invention relates to the vectorized compounds comprising a compound of formula (II) or (VI) as defined above coupled to at least one biovector via the optional intermediary of a bonding group, it being possible for this biovector to be a targeting biovector for a pathological region. This is because, although it has been explained that the compounds of formula (II) or (VI) are particularly advantageous as non-specific compounds, it will also be possible to use them as signal entity for specific compounds, for example by coupling them to targeting biovectors. The advantage of the relaxivity, of the stability, of the solubility of the monomer is thus combined with use as specific product.

The bonding group can be bonded to the compounds of formula (IIa) at D or $F_1$ and the optional bonding group or the biomolecule, in the case of the absence of the bonding group, can be bonded to the compounds of formula (II) at X1 to X3. In this case, at least one of the X1 to X3 groups is a biomolecule or a functional group capable of being bonded to a biomolecule; or D or $F_1$ is a functional group capable of being bonded to a biomolecule.

The optional bonding group or the biomolecule, in the case of the absence of the bonding group, can be bonded to the compounds of formula (VI) at X1 to X5. In this case, at least one of the X1 to X5 groups is a biomolecule or a functional group capable of being bonded to a biomolecule.

Numerous biovectors which can be used are disclosed, for example, in the document WO 2004/112839, in particular pages 60 to 82 and in particular numbers 1 to 27, the coupling of the biovectors with chelates being exemplified, for example, in this document, in particular pages 135-137, incorporated by reference.

The Applicant has thus studied compounds of formula (VIIIa), written: $(II)_r$-(bonding group)$_s$-(biovector)$_t$, and (VIIIb), written: $(VI)_r$-(bonding group)$_s$-(biovector)$_t$, with typically r, s and t between 1 and 5.

Numerous other biovectors which can be used have been disclosed, for example, in WO 2005/049005, WO 2005/049095, WO 2005/042033 and WO 2001/9188: biovectors targeting VEGF and angiopoietin receptors, polypeptides targeting fibrin, peptides for targeting integrins, peptides for targeting metalloproteases (MMP), peptides targeting, for example, the KDR/Flk-1 receptor or the Tie-1 e receptors, ligands for targeting G-protein receptors GPCRs, in particular cholecystokinin, RGD peptides, agents for targeting amyloid deposits, cathepsin-cleaved peptides, angiogenesis inhibitors, targeting biovectors for P-selectin or for E-selectin, tyrosine kinase inhibitors, somatostatin analogues, peptides for targeting GRP or bombesin receptors, biovectors given in *Topics in Current Chemistry, vol. 222*, 260-274, *Fundamentals of Receptor-based Diagnostic Metallopharmaceuticals*, and in particular:

targeting biovectors for peptide receptors overexpressed in tumours (LHRH receptors, bombesin/GRP, VIP receptors, CCK receptors, tachykinin receptors, for example), in particular somatostatin analogues or bombesin analogues, octreotide-derived peptides which are optionally glycosylated, VIP peptides, α-MSHs, CCK-B peptides;
peptides chosen from: cyclic RGD peptides, fibrin alpha-chain, CSVTCR, tuftsin, fMLF, YIGSR (receptor:laminin).

Use may in particular be made of vectors for targeting integrins having a specificity of greater than 1000, preferably of greater than 10 000, 100 000 or more, which have a possible use in MRI or in scintigraphy, for example mentioned in: *J. Med. Chem.*, 2003, 46, 4790-4798, *Bioorg. Med. Chem. Letters*, 2004, 14, 4515-4518, *Bioorg. Med. Chem. Letters*, 2005, 15, 1647-1650.

As regards the peptides, the preparation, the optional cyclization and the coupling with chelates are disclosed, for example, in US 2004/0210041, in particular pages 15 to 20 for coupling of chelates with two different peptides.

A large number of bonding groups can be used, in so far as they are capable of interacting with at least one functional group of the biovector and at least one functional group of compounds of formula (II) or (VI). Mention will in particular be made of:

A) $-(CH_2)$-2-phenyl-NH, $-(CH_2)_3$-NH, -NH$-(CH_2)_2$-NH, -NH-$(CH_2)_3$-NH, nothing or a single bond B) P1-1-P2, which are identical or different, P1 and P2 being chosen from O, S, NH, nothing, $-CO_2$, -NCS, -NCO, $-SO_3H$, -NHCO, -CONH, -NHCONH, -NHCSNH, $-SO_2NH-$, -NHSO$_2-$ or squarate with 1=alkylene, alkoxyalkylene, polyalkoxyalkylene, alkylene interrupted by phenylene, alkylidene or alcilidene C) bonding groups disclosed in U.S. Pat. No. 6,264,914, capable of reacting with the amino, hydroxyl, thiol, carboxyl, carbonyl, carbohydrate, thioether, 2-aminoalcohol, 2-aminothiol, guanidinyl, imidazolyl or phenol functional groups (of the biovector and of the compound of formula (II) or (VI)).

Groups capable of reacting with thiol groups include α-haloacetyl compounds of the $-Z-CH_2CO-$ type (where Z=Br, Cl or I), which can also be used to act with thioether, phenol or amino groups.

Groups capable of reacting in particular with amino groups include:

alkylating compounds: α-haloacetyl compounds, N-maleimide derivatives, aryl compounds (for example nitrohaloaromatic compounds), aldehydes and ketones capable of formation of Schiff bases, epoxide derivatives, such as epichlorohydrin, chlorine-comprising triazine derivatives which are highly reactive with regard to nucleophiles, aziridines, squaric acid esters or α-haloallyl ethers.

acylating compounds: isocyanates and isothiocyanates, sulphonyl chlorides, esters, such as nitrophenyl esters or N-hydroxysuccinimidyl esters, acid anhydrides, acylazides, azolactones or imidoesters.

Groups capable of reacting with carboxyl groups include diazo compounds (diazoacetate esters, diazoacetamides), compounds which modify carboxylic acids (carbodiimides, for example), isoxazolium derivatives (nitrophenyl chloroformate; carbonyldiimidazoles, and the like) or quinoline derivatives.

Groups capable of reacting with guanidinyl groups include dione compounds, such as phenylenediglyoxal, or diazonium salts.

D) bonding groups disclosed in U.S. Pat. No. 6,537,520 of formula

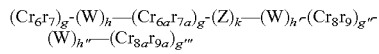

with the meaning disclosed in this document.

E) bonding groups disclosed in WO 2005/009393, pages 17 to 20.

The Applicant has also studied the compounds of formula (VIIIa) or (VIIIb) indicated above comprising a biological targeting biovector part such that it undergoes in vivo a modification in structure which modifies the relaxivity of the compound. This modification, described in the prior art as SMART concept, takes place, for example, by virtue of an enzymatic cleavage (proteases (metalloproteases, caspases, cathepsins, and the like), lipases, nucleases, and the like) or local physicochemical modifications in a pathological region.

The invention also relates to a method for screening specific compounds of formula (II) or (VI) having a high affinity which comprises preparing the compounds comprising a targeting part, bringing into contact with a biological target and measuring the bonding (in particular dissociation constant) with the target.

In another particularly advantageous aspect, the present invention relates to a complex of a compound of formula (II) or (VI) according to the present invention, of a multimer according to the present invention or of a vectorized compound according to the present invention, advantageously of formula (VIIIa) or (VIIIb), with M, M representing an ion of a paramagnetic metal of atomic number 21-29, 42-44 or 58-70 (for example, scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium; the elements Gd(III), Mn(II), europium and dysprosium are particularly preferred), or a radionuclide chosen from $^{99}$Tc, $^{117}$Sn, $^{111}$In, $^{97}$Ru, $^{67}$Ga, $^{68}$Ga, $^{89}$Zr, $^{177}$Lu, $^{47}$Sc, $^{105}$Rh, $^{188}$Re, $^{60}$Cu, $^{62}$Cu, $^{64}$Cu, $^{67}$Cu, $^{90}$Y, $^{159}$Gd, $^{149}$Pr and $^{166}$Ho, or an ion of a heavy metal of atomic number 21-31, 39-49, 50, 56-80, 82, 83 or 90.

Advantageously, the complex according to the present invention is such that M is an ion of a paramagnetic metal chosen from $Gd^{3+}$, $Mn^{2+}$ and $Fe^{3+}$, advantageously $Gd^{3+}$. Advantageously, the complex according to the present invention is chosen from the complexes of following formulae:

1

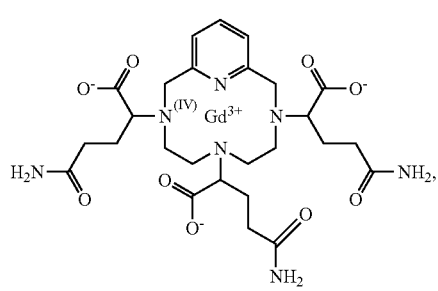

2

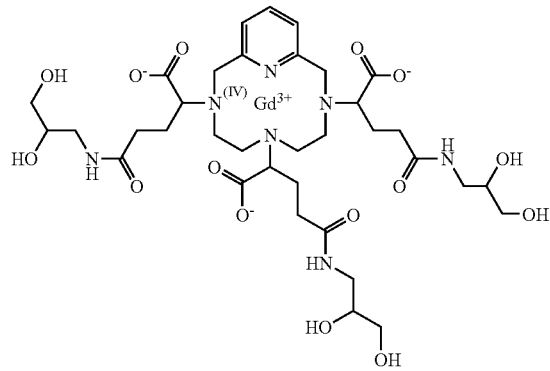

3

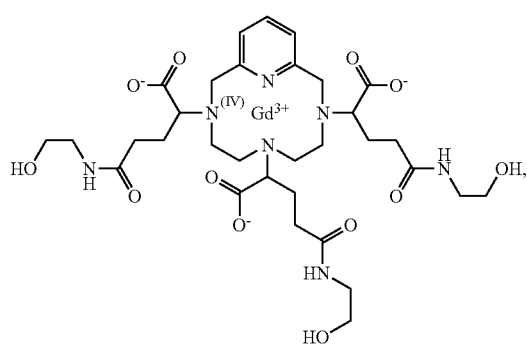

4

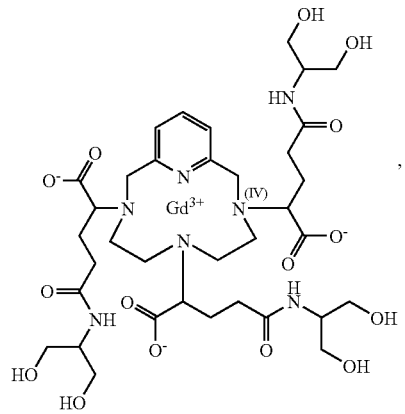

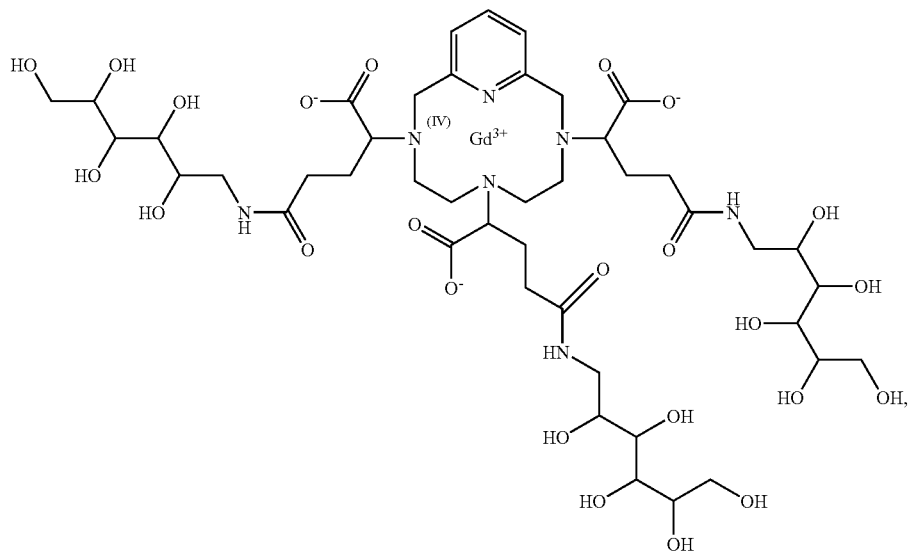
5
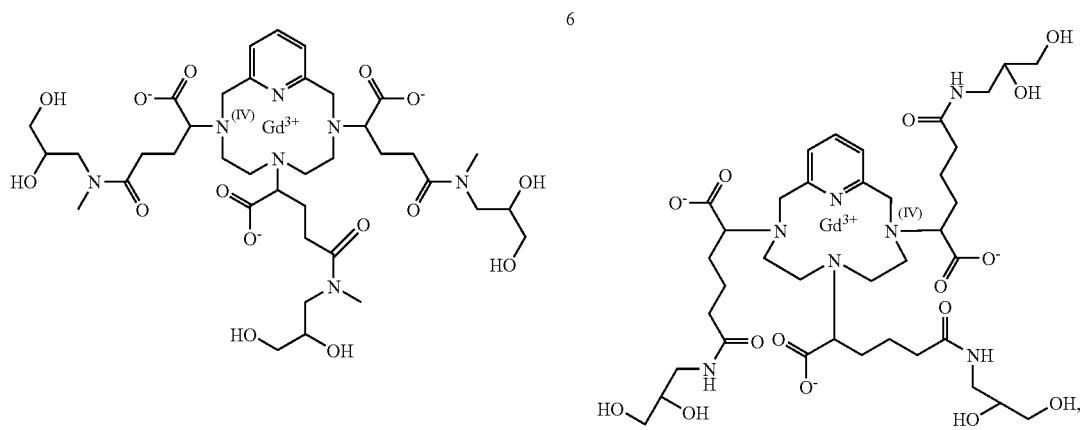
6
7
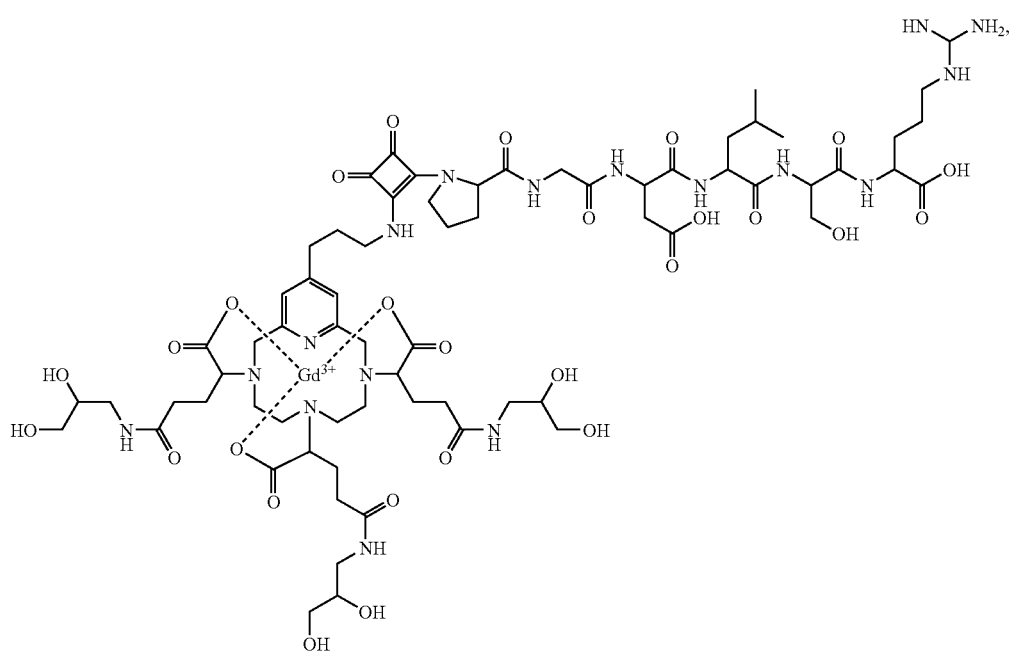
10a

-continued
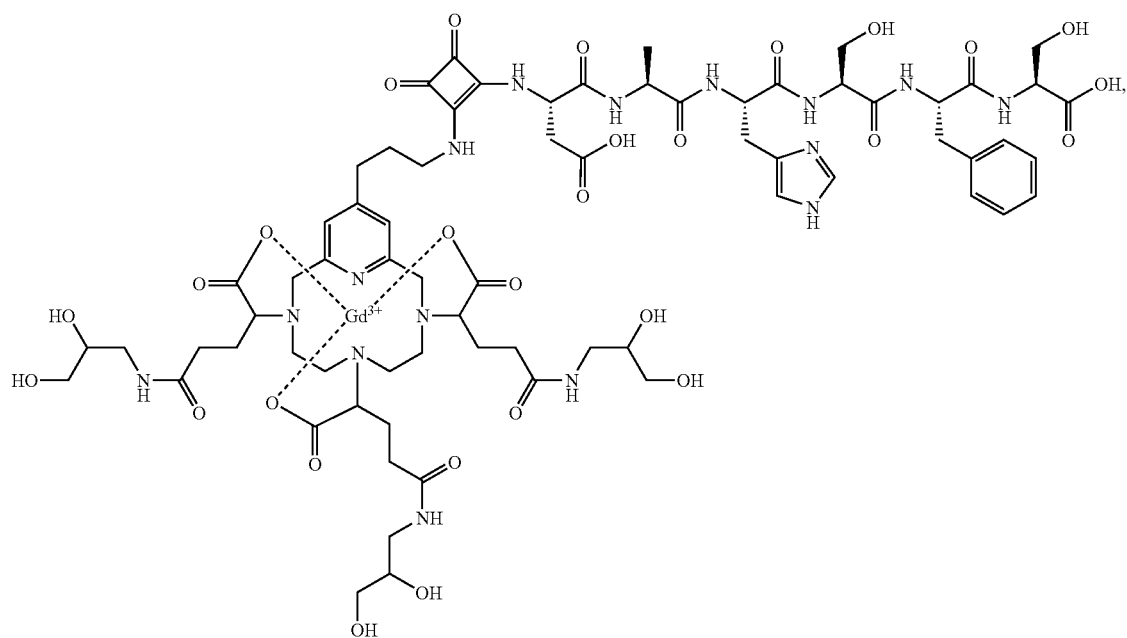
10b
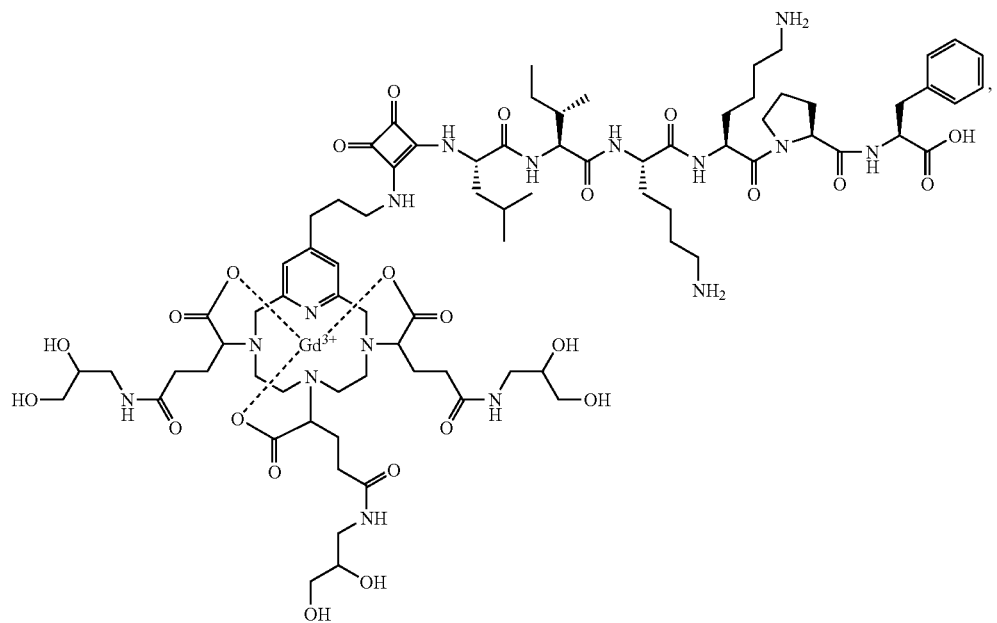
10c
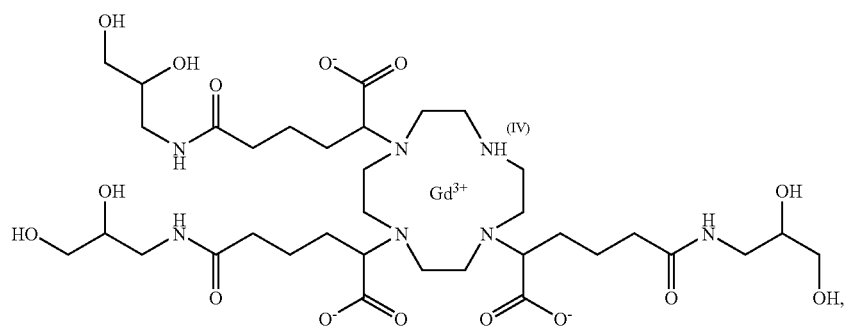
11

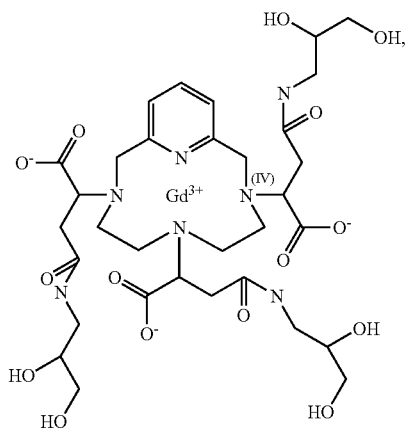

13

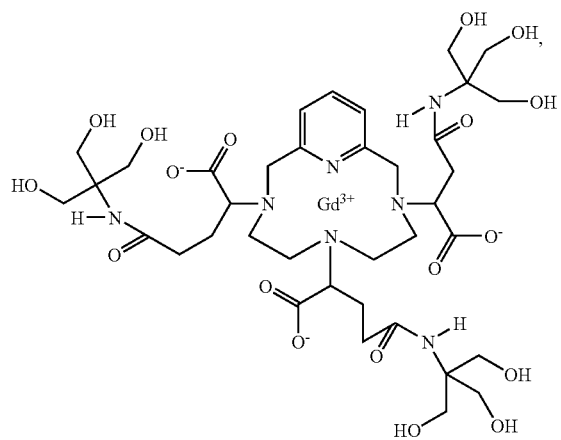

18

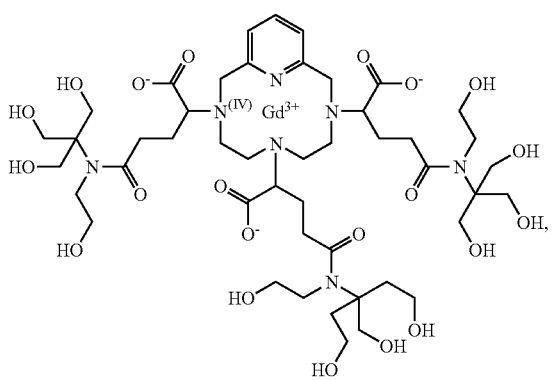

19

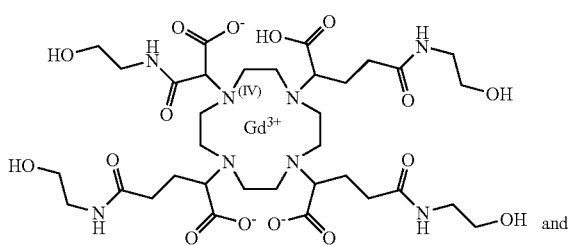

15

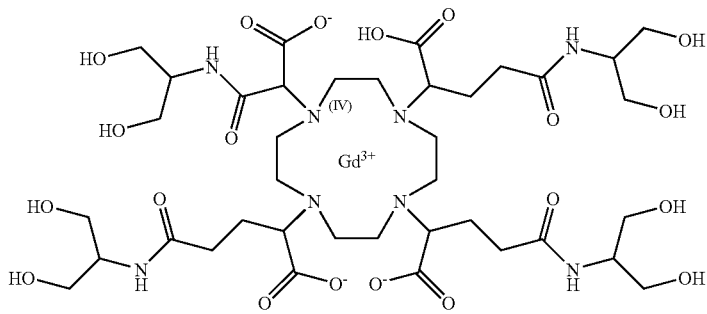

17

The invention relates in particular to the complexes of compounds (II) according to the present invention which are nonionic and which exhibit:

- a relaxivity in water of at least 9 mM$^{-1}$s$^{-1}$Gd$^{-1}$, preferably at least 10, 12, 14 mM$^{-1}$s$^{-1}$Gd$^{-1}$,
- an osmolality of between 800 and 1200 mOsm/kg, advantageously of the order of 900 to 1100, advantageously about 1000 mOsm/kg (Wescor 5220 tonometer, Bioblock), for a Gd concentration of 400 to 600 mM advantageously of about 500 mM.
- a molecular weight of between 800 and 1300, in particular between 950 and 11001,
- a viscosity of less than 10 mPa·s (Anton Paar AMVn viscometer), advantageously of between 2 and 5 mPa·s.

The comparison between a complex with Gd$^{3+}$ according to the present invention and the products of the prior art is shown in the following table.

| PRODUCT | Administration dose of the product in man | Relaxivity r1 at 60 MHz in water | Osmality (mOsm/kg) |
|---|---|---|---|
| Dotarem ® | 500 mM | 3.5 mM · s$^{-1}$ · Gd$^{-1}$ | 1350 |
| Magnevist ® | 500 mM | 3.5 mM · s$^{-1}$ · Gd$^{-1}$ | 1950 |
| Gadovist ® (1M) | 1000 mM | 3.5 to 4.5 mM · s$^{-1}$ · Gd$^{-1}$ | 1400 |
| Complex of the compounds (II) with Gd$^{3+}$, | 500 mM | 10 to 15 mM · s$^{-1}$ · Gd$^{-1}$ | 1000 |

The relaxivity is multiplied by a factor of approximately 3 in comparison with the commercial products administered according to the same dose of product, as it happens a dose of approximately 500 mM (typically an injectable dose of 15 ml for Dotarem®).

For the same injected dose of gadolinium, the compounds are twice as effective as Gadovist®, which can be administered at 1M (that is to say, twice as concentrated as Dotarem®), this result being obtained by comparison of the products (4×1000) for Gadovist® and of the products (11×500) for the complexes of the compounds (II). The satisfactory viscosity of the complexes of the compounds (II) makes it possible to use them clinically at a concentration of 500 mM, in contrast to the compounds of PCTA type which carry heavy chains and have a high viscosity, it not being possible for their concentration to range beyond approximately 150 mM.

Among the complexes of the compounds (II), the complexes of the compounds (II) for which the relaxivity r1 is substantially stable between 40 MHz (1 T) and 300 MHz (7 T) are particularly advantageous. The term "relaxivity substantially stable between 40 MHz and 300 MHz" is understood to mean a maintenance of or a fairly small fall in relaxivity, the fall not exceeding 20%, preferably not exceeding 10 to 20%.

This combination of preferred ranges of the above parameters does not, however, exclude outstanding complexes undergoing a greater fall in relaxivity r1, for example of 30% for high fields of the order of 3 to 7 tesla, when this parameter of stability at high fields is compensated for by other physicochemical characteristics highly advantageous for the clinical use of the said complex. This is the case with the complex 7 according to the present invention in particular, for which the relaxivity is 14.7 mM$^{-1}$s$^{-1}$ Gd$^{-1}$ at 20 MHz, 12.8 at 40 MHz, 10.4 at 300 MHz. This complex will thus be very effective for MRI devices between 1 and 3 T, which represent an important part of the pool of devices.

The Applicant has additionally found, surprisingly, an increase in relaxivity of the complexes of the compounds (II) around 60 MHz (1.5 T) with r1 values of the order of 12 to 15 mM$^{-1}$s$^{-1}$ Gd$^{-1}$, which thus makes them very effective for clinicians. The increase in relaxivity between 20 MHz and 60 MHz is approximately 20%.

Particularly advantageous compounds (II) (in particular compound 2 described in detail above) are those which exhibit a stable relaxivity even in physiological conditions with the presence of ions without the unwanted quench effect due to endogeneous ions.

Surprisingly, the Inventors have discovered that the relaxivity of the complexes according to the present invention (carrying short amino alcohol chains) is markedly better than that of compounds comprising a PCTA backbone grafted with short alcohol chains.

The Applicant has thus compared the results obtained in comparison with compounds of the document U.S. Pat. No. 5,403,572, which exhibit short alcohol chains and not short aminoalcohol chains.

Thus, the compound of Comparative Example 8 according to the prior art (—CH(CO$_2$H)—CH$_2$OH branch) has a relaxivity only of 4.7, due probably to undesirable folding over of the branch, which interferes with the exchanges of water of the chelate (barrier of the exchange with the ring of one of the two water molecules). The compound of Comparative Example 9 according to the prior art (—CH(CO$_2$H)—CH$_2$—CH$_2$OH branch) has a relaxivity only of 6.

The results of comparison with prior art are collated in Table 2 below.

| Product | Relaxivity r1 in water (mM − 1s − 1) at 0.5 T |
|---|---|
| Complexes of the compounds II (Examples 2 to 7 and 11) | r1 = 10 to 15 |
| Compound 2 | r1 = 11 (MW = 970 MW/r1 = 88 osmolality = 1000) |

-continued
| Product | Relaxivity r1 in water (mM − 1s − 1) at 0.5 T |
|---|---|
| Comparative Example (prior art) without coupling to short aminoalcohol chains | 7.2 |
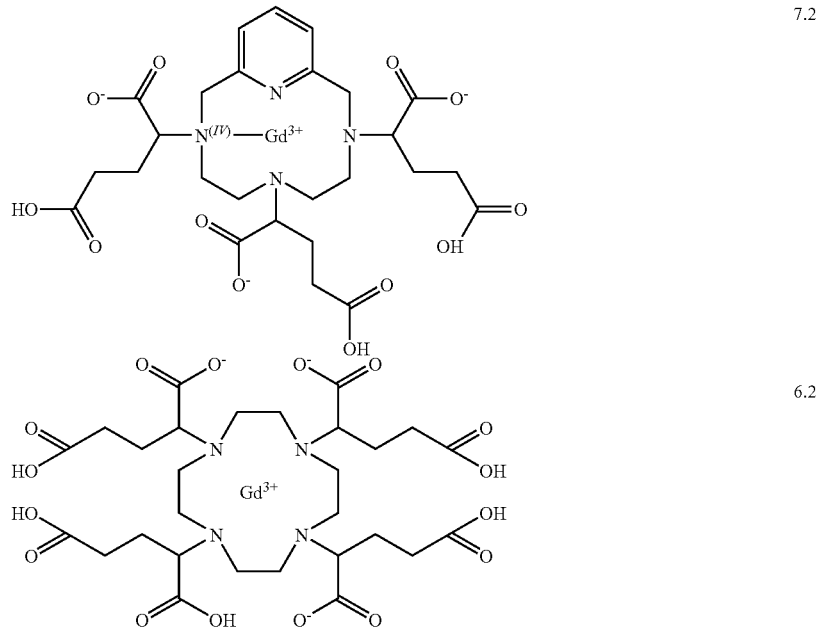
Comparative Example 8 (prior art)
6.2
5
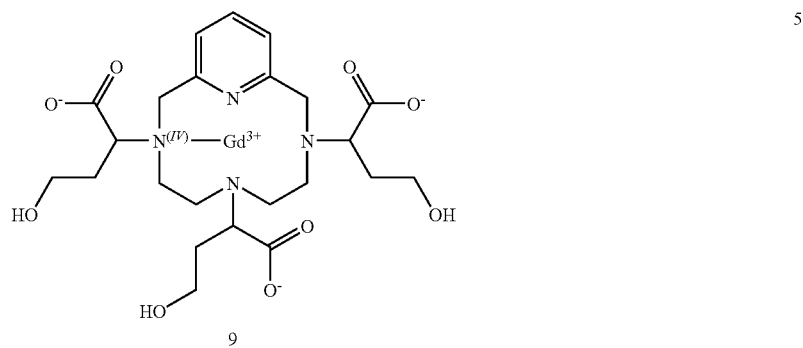
Comparative Example 9 (prior art)
Compound with a DOTA core carrying aminoalcool groups with a molecular weight greater than 200
6
r1 = 14
(MW = 2000)
MW/r1 = 140)
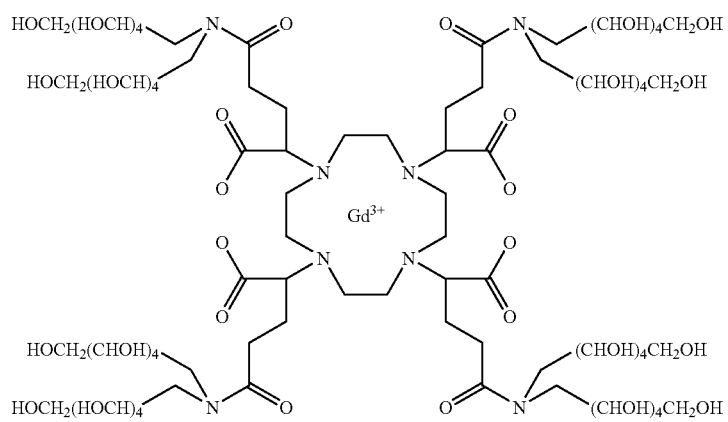

This table also reflects the very advantageous mass efficiency (ratio MW/r1=molecular weight/relaxivity) of compounds II. Notably compounds II.a with PCTA core have in combination very good relaxivity, optimised mass efficiency ratio (in the order of 90) and low osmolality.

The compounds of the invention are highly advantageous in comparison with known products which are complex or not very stable or of excessively high osmolality, in particular:
  chelates carrying long chains presenting problems of viscosity and of manufacturing costs,
  chelates comprising a targeting part which is intended for the coupling in the patient of the injected product with biological macromolecules, such as albumin; the in vivo coupling being reflected by an increase in relaxivity by an effect of immobilization of the chelate.

Thanks to their non ionicity, compounds II having an osmolality in order of 1000 which is to compare with about 1400 and 2000 for ionic (respectively one and two free COOH groups) compounds. In practice this allows to concentrate the injected solution, namely to inject much less product volume (ratio 1400/1000 and 2000/1000 respectively) to the patient, which is very advantageous for their comfort. In practice, for instance 15 ml of compound II is injected instead of 20 ml for Dotarem or other compounds of the prior art and the relaxivity is at least twice better.

The complexes of the compounds (II) obtained are therefore entirely appropriate as non-specific contrast agents (not vectorized by a biological targeting biovector entity; nevertheless they are useful in many diagnostic indications such as angiography, CNS central nervous system and variants). Furthermore, they can be sterilized.

The present invention additionally relates to a pharmaceutical composition comprising a compound according to the present invention or a multimer according to the present invention or a vectorized compound according to the present invention or a complex according to the present invention, a pharmaceutically acceptable vehicle and optionally formulation additives.

The present invention relates in particular to a lipid pharmaceutical composition comprising a compound according to the present invention or a multimer according to the present invention or a vectorized compound according to the present invention or a complex according to the present invention bonded to a lipid nanoparticle. Advantageously, these lipid compositions are emulsions of liposomes type, of micelles or analogous lipid particles. In these compositions, preferably, the compound, multimer or complex according to the present invention is modified in order to exhibit at least one lipophilic group for bonding to the lipid particle. This compound, this multimer or this complex are thus coupled, advantageously by chemical coupling with an appropriate lipophilic transporter, to lipid particles or lipid encapsulation systems preferably chosen from liposomes, fluorocarbon nanoparticles, oil emulsions and micelles.

The compounds of formula (II) or (VI) can be rendered lipophilic at the groups X1 to X5, by choosing at least one of the X1 to X5 groups from lipophilic groups, such as $-(CH_2)_a-CONR_{11}R_{12}$, or

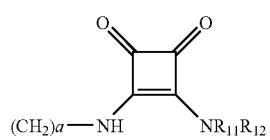

groups, in which a=1, 2 or 3, $R_{11}$ and $R_{12}$ independently represent an H atom or a saturated or unsaturated, linear or branched, substituted or unsubstituted $C_7$-$C_{30}$ alkyl chain optionally interrupted by a double bond, O, NH, $NR_{13}$ or S, where $R_{13}$ is a $C_1$-$C_3$ alkyl, or $R_{11}$ and $R_{12}$ independently represent a

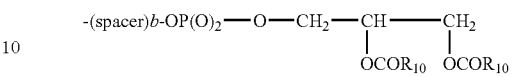

group with b=0, 1 or 2 and $R_{10}$ a saturated or unsaturated group of at least 6 carbon atoms which is optionally substituted, the spacer representing a $-CH_2CH_2$ or polyalkylene glycol group, phosphatidylethanolamine or a peptide derivative, such as serine.

The present invention also relates to the diagnostic compositions, in particular the contrast agents, more particularly a diagnostic composition for magnetic resonance imaging, comprising a compound according to the present invention or a multimer according to the present invention or a vectorized compound according to the present invention or a complex according to the present invention.

A process for the preparation of a metal complex according to the present invention of a compound of formula (IIa) in which X1 to X3 independently represent $-(CH_2)_n-CO-NR7R8$, in which n=1 to 3 and R7 and R8 are as defined above, comprises the stages:

a) reacting the condensed macrocycle of following formula (IV)

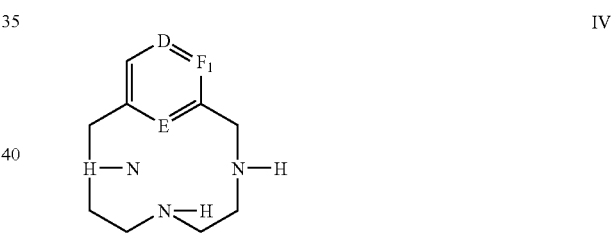

IV in which D, E and $F_1$ are as defined above, with a compound of formula R'OOC—CHQ-$(CH_2)_n$—COOR', in which n=1 to 3, Q represents a leaving group, advantageously a halogen atom, preferably bromine, or a ($C_1$-$C_3$)alkylsulphonate, tosylate or triflate group, and R' represents H or a ($C_1$-$C_3$)alkyl or benzyl group, in order to obtain the hexaacid or ester of following formula (V)

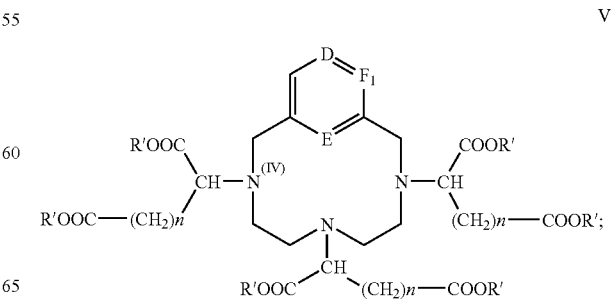

V b) optionally hydrolysing or hydrogenating the ester functional groups of the hexaacid of formula (V) when R' is other than H, in order to obtain the hexaacid of formula (Va)

Va

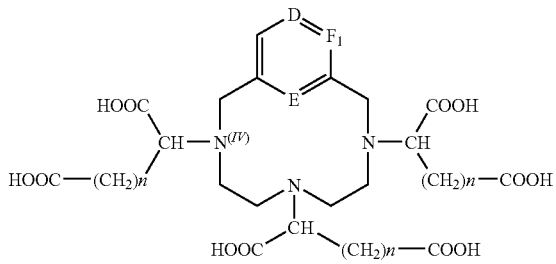

in which D, E and $F_1$ are as defined above and n is between 1 and 3;

c) reacting the hexaacid of formula (Va) with a salt or an oxide of the metal to be complexed, in order to obtain the corresponding complex or one of its salts with a base;

d) reacting the complex, in the presence of an agent which activates carboxylic acid functional groups, with the aminoalcohol group or groups NHR7R8, in which R7 and R8 are as defined above, in order to obtain the triamide of formula (IIa), in which X1 to X3 independently represent —$(CH_2)_n$—CO—NR7R8 in which n=1 to 3 and R7 and R8 are as defined above.

The macrocycle of formula (IV) can be prepared by the method of Richman and Atkins described in *Inorg. Chem.*, 32, 5257-5265 (1993).

The substitution of the nitrogen atoms (stage (a)) is carried out, for example, by the action of an α-bromoglutaric ester in the presence of an inorganic or organic base, such as NaOH, $Na_2CO_3$ or $N(C_2H_5)_3$, in solution in a polar solvent, such as an alcohol or, preferably, an aprotic solvent, such as acetonitrile or tetrahydrofuran.

The hydrolysis of the ester functional groups (stage (b)) is advantageously obtained by the action of a base or of an acid in an aqueous or aqueous/alcoholic medium.

The complexing (stage (c)) is carried out conventionally, for example as disclosed in U.S. Pat. No. 5,554,748 or in *Helv. Chim. Acta*, 69, 2067-2074 (1986).

In particular, in order to obtain the gadolinium complex, $GdCl_3$ or $Gd_2O_3$ can be reacted with the compound of formula (V) in aqueous solution at a pH of between 5 and 6.5. It is also possible to exchange the cation of a complex of formula (Va) or (II), when the relative stability of the two complexes allows it, in particular with an ion-exchange resin.

The amidation reaction (stage (d)) can be obtained in an aqueous medium, optionally in the presence of a third solvent, such as dioxane or tetrahydrofuran, with an activating agent, such as a soluble carbodiimide, for example those carrying an amine group disclosed in *J. Org. Chem.*, 21, 439-441 (1956) and 26, 2525-2528 (1961) or U.S. Pat. No. 3,135,748 or carrying a quaternary ammonium group disclosed in *Org. Synth.*, V, 555-558, which relates to 1-ethyl-3-(3-dimethylamino)carbodiimide (EDCI) and 1-cyclohexyl-3-(2-morpholinoethyl)carbodiimide metho-p-toluenesulphonate. It can also be carried out with N-hydroxysulphosuccinimide, as described in *Bioconjugate Chem.*, 5, 565-576 (1994), or 2-succinimido-1,1,3,3-tetramethyl-uronium tetrafluoroborate and analogues, described in *Tetrahedron Letters*, 30, 1927-1930 (1989).

Another process according to stage (d) consists in forming an intermediate activated ester by reacting, for example, N-hydroxysulphosuccinimide (NHS) or hydroxybenzotriazole (HOBT) in the presence of carbodiimide, such as EDCI, with the complex (Va), which can be dissolved by salification with an inorganic cation, for example an ammonium or sodium.

With 2-ethoxy-1-ethoxycarbonyl-1,2-dihydroquinoline (EEDQ), the reaction can be carried out in an aqueous/alcoholic medium. The amines NHR7R8 are known compounds available commercially or can be prepared by processes well known to a person skilled in the art.

According to another aspect, the invention relates to a diagnostic method and to a radiopharmaceutical treatment method using a complex as described above.

According to another aspect, the invention relates to the use of a compound or complex as described above in the preparation of a diagnostic or radiopharmaceutical composition.

For MRI diagnosis, the intravenous administration by injection, usually in solution, typically takes place at a dose of 1 to 500 μmol Gd/kg. The unit doses will depend on the nature of the contrast product, on the administration route and on the patient and in particular on the nature of the disorder to be studied. For intravenous injection and observation by magnetic resonance, the concentration of the solution will typically be between 0.001 and 1 mole/liter and, as the case may be, from 0.001 to 0.3 millimole/kilo will be administered to the patient. The contrast products comprising the complexes according to the present invention are intended in particular for imaging the brain, organs, such as the heart, liver or kidneys, all or part of the vascular system (coronarography, angiography, and the like), and for studying the perfusion of these regions and characterizing the anomalies in tumour, inflammatory or ischemic permeability.

For radiopharmaceutical diagnosis, the intravenous administration by injection, usually in saline solution, typically takes place at a dose of 1 to 100 mCi per 70 kg of body weight, preferably of 5 to 50 mCi.

The choice of the radionuclide depends in particular on its half life (generally from 0.5 to 8 days), on the emission energy of the radionuclide (in particular β-emitting radionuclides). The radioisotope is incorporated by appropriate known methods. For 99 mTc, a general protocol is given in WO 2005/009393, pages 25-26, in the case of a peptide: the peptide-bonding group-chelate non-metallic conjugate is dissolved, when there is an SH group in the peptide, use is made of a group which protects the thiol group from oxidation, the labelling used is sodium pertechnetate and a reducing agent to reduce the technetium, the labelled conjugate obtained is separated. A protocol with transchelation is given on page 26.

It should be remembered that it is also possible to label the chelate before coupling with the biovector. For example, for $^{111}$In and $^{177}$Lu, a solution comprising 30-150 μg of biovector (peptide)-bonding group-chelate non-metallic conjugate and 20 mCi of $^{177}$LuCl$_3$ is prepared. The pH is adjusted, for example to 6. The solution is incubated at ambient temperature for 60 minutes. The non-complexed $^{177}$Lu is chelated by adding an $Na_2$EDTA solution. The formation of the labelled complexes is evaluated on an ion-exchange chromatography column, for example Sephadex C25. The solution prepared is adjusted to the physiological pH.

For use as X-ray contrast agents, the heavy atom concentration is typically from 0.1M to 5M, with concentrations by intravenous administration of the order of 0.5 to 1.5 mmol/kg.

According to another aspect, the invention relates to the use of a complex as described above in the preparation of a composition intended for optical imaging.

The invention also relates to an imaging method comprising the synthesis of a complex comprising a paramagnetic metal according to the invention, its administration to a patient and MRI imaging. The invention also relates to an imaging method comprising the synthesis of a radiopharmaceutical complex according to the invention capable of targeting a pathological region, its administration to a patient and imaging by SPECT or planar γ scintigraphy or positron emission tomography (PET method).

The invention also relates to compositions comprising a complex according to the present invention for magnetic resonance imaging, when M represents a paramagnetic cation, or for nuclear medicine, when M represents a radioelement, or for radiology, when M is the cation of a heavy atom which absorbs X-rays, it being possible for the said compositions to comprise the usual additives and vehicles for administration by the oral or parenteral route.

More generally, the usual conditions for diagnostic use or optionally therapeutic use (in radiotherapy) which can be used for the complexes according to the present invention are given in WO 2005/062828, in the parts "Diagnostic and Therapeutic Uses" and "Radiotherapy".

In the case of radionuclides for imaging by PET, PET-SCAN or analogous method, the synthesis of which is possible at the time of use other than close to the site of injection of the product into the patient, it will be advantageous to use a biovector (for example somatostatin) coupled to a compound (II) or (VI) or any other compound used in PET (for example NOTA) exhibiting a "transparent" behaviour with respect to the biovector. More specifically, this transparency consists in the compound not significantly interfering with the recognition (the affinity) of the biovector for its biological target. This transparency is promoted by the hydrophilic groups of the aminoalcohol chains, which are capable of masking the compound, even when it is in the complex form. A screening test on the affinity of the biovector with various structures and lengths of chains of hydrophilic nature can thus make it possible to select satisfactory products of formula (VIII). Moreover, the desired masking effect can be studied for other chemical groups than aminoalcohols.

This protective effect on the biovector will be highly advantageous in particular in the case of gallium $^{68}$Ga, which an appropriate extemporaneous preparation protocol (protocol in particular of Maecke et al. from germanium $^{68}$Ge, making it possible to very markedly improve the use of the radionuclide) is known to a person skilled in the art. The coupling of the compound with the gallium (for example disclosed in U.S. Pat. No. 6,071,490 with a DTPA-peptide conjugate) is carried out using, for example, 10-100 mCi of $^{68}$Ga. Appropriate bonding groups between the compound and the biovector can also be chosen in order to facilitate the desired masking effect which protects the affinity. In particular, according to one implementation, use is made of a hydrophilic bonding group (PEG derivative, for example). The size of the bonding groups will advantageously be sufficiently long to move the compound away from the region or regions of the biovector which interacts with the biological target.

The invention also relates to medical imaging methods which consist in administering, to the patient, a composition comprising a complex of a compound of formula (II) or (VI) according to the present invention and in observing the region to be studied obtained by magnetic resonance, by scintigraphy or under X-rays.

The diagnostic compositions of the invention can comprise, with a complex of the invention, additives, such as antioxidants, buffers, osmolality regulators, stabilizing agents, salts of calcium, magnesium or zinc, or small proportions of other chelates of these cations or of complexing compounds. Formulation examples appear in the general works and in particular in *Remington's Pharmaceutical Science*, 18th Edition (1990), Mack. Pub. It is possible, for example, to prepare sterile saline or aqueous solutions comprising formulation adjuvants (lactose, methylcellulose, mannitol) and/or surfactants (lecithins, Tween®, and the like).

For nonionic complexes (such as, for example, the complexes of the compounds of formula (II) according to the invention), use may be made of excipients, for example mannitol.

A pharmaceutically acceptable dose refers to a dose appropriate for a therapeutic or diagnostic use.

The invention, unless otherwise mentioned, covers all the chiral, diastereoisomeric, racemic, in particular cis-trans, R—S, L-D, forms of the compounds described.

In addition to the compounds (II) described above, the Applicant has studied chelates of formula:

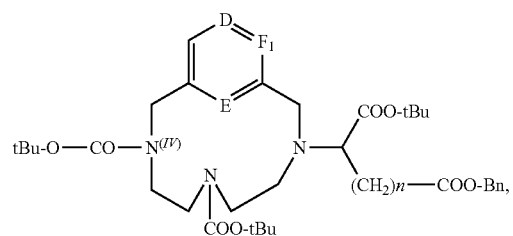

(A1)

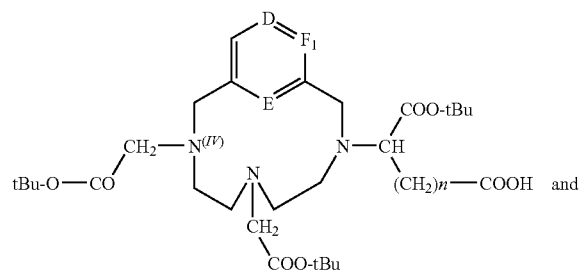

(A2)

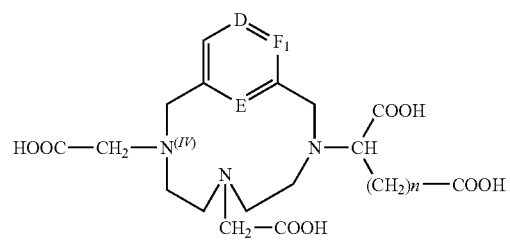

(A3)

in which D, E and $F_1$ are as defined above, the organic chelate (or the composition comprising this organic chelate) exhibiting an enantiomeric excess, that is to say having more than 50% of the (R) isomer or of the (S) isomer, of the chelate. In particular, n will be between 1 and 4, especially n=2, and there will be present an excess of at least 80, 85, 90 or 95% of one of the two isomers. Such an excess can be advantageous in obtaining enriched or optically pure contrast agents possessing improved relaxivity.

For (A1), the

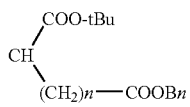

group can be connected to any of the three nitrogen atoms.

For (A2), the

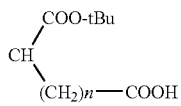

group can be connected to any of the three nitrogen atoms.

For (A3), the

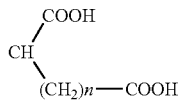

group can be connected to any of the three nitrogen atoms.

Such compounds can be used for the synthesis of compounds coupled to biovectors, as is disclosed for DOTAs in Examples 4 and 5 of the document WO 2005/001415.

More generally, the Applicant has studied any chelate to which short aminoalcohol chains are grafted. These chelates are, for example, DOTMA, NOTA, TETA, TTHA, CYDTA, HPDO3A, PA-DOTA, MeO-DOTA, MXDTPA, DTPA, PDTA, MECAM, CMDOTA, CDTA, CDTPA or OTTA type, AAZTA (Inorganic Chemistry, vol 43, no 24, 2004, 7588-7590) and any derivative thereof being coupled top aminoalcohol chains directly or by linkers), the nomenclature of which is known, whatever the isomerism of the chelates.

Furthermore, the Applicant has studied compounds possessing a PCTA backbone, of formula

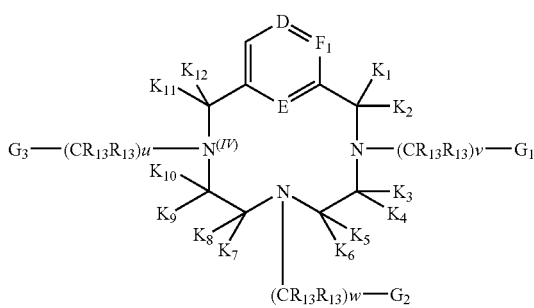

(VII)

in which:

u, v and w are independently 1 or 2;

each $R_{13}$ is chosen independently from the group:

H, alkyl, alkoxy, cycloalkyl, aryl, aralkyl, alkylamino, alkanoyl or alkanoyloxy, it being possible for each to be substituted, or represents a functional group capable of forming a conjugate with a biomolecule or of forming a multimer of this compound of formula (VII) or a functional group forming a conjugate with a biomolecule; $G_1$, $G_2$ and $G_3$ independently represent —COOR14, —P(O)(OR14)$_2$, —P(O)(OR14)(R14), —C(O)N(R14)$_2$ or —R15-P(O)—OR14 (phosphinates in which each R14 is H and each R15 is a ($C_1$-$C_4$)alkyl or an arylalkyl);

each $K_1$ to $K_{12}$ is chosen independently from: H, alkyl, hydroxyalkyl, alkoxyalkyl or a functional group capable of forming a conjugate with a biomolecule or of forming a multimer of this compound of formula (VII).

In the formula (VII), the following definitions apply:

"cycloalkyl" refers to a cyclic hydrocarbon group of 3 to 8 carbon atoms. The groups may be unsubstituted or substituted, for example by: alkyl, halogen, hydroxyl, hydroxyalkyl, alkoxy, alkanoyl, alkanoyloxy, amino, alkylamino, dialkylamino, alkanoylamino, thiol, alkylthio, nitro, cyano, carboxyl, carbamoyl, alkoxycarbonyl, alkylsulphonyl, sulphonamido and the like;

"alkoxy" refers to -alkyl(O);

"aryl" refers to phenyl, pyridyl, furyl, thiophenyl, pyrrolyl, imidazolyl and the like. Preferred substituted aryl groups are substituted by 1, 2 or 3 halogens, nitroamino, maleimido, isothiocyanato, hydroxyl, hydroxyalkyl, alkyl, alkoxy, carbamoyl, carboxamido, acylamino or carboxyl;

"aralkyl" refers to an aryl group bonded to an alkyl group;

"halogen" refers to bromo, chloro, fluoro or iodo;

"alkanoyl" refers to alkyl-(C=O)—;

"alkanoyloxy" refers to alkyl-(C=O)—O—;

"alkylamino" refers to —NHR with R an alkyl.

Throughout the text, a hydroxyalkyl group refers to a linear or branched alkyl chain comprising one or more hydroxyl groups.

The invention will be illustrated with the help of the following nonlimiting examples.

Relaxivity Measurements:

The relaxation times T1 and T2 were determined by standard procedures on a Minispec 120 device (Bruker) at 20 MHz (0.47T) and 37° C. The longitudinal relaxation time T1 is measured using an inversion recovery sequence and the transverse relaxation time T2 is measured by a CPMG technique.

The relaxation rates R1 (=1/T1) and R2 (=1/T2) were calculated for different total metal concentrations (varying from $0.1 \times 10^{-3}$ to $1 \times 10^{-3}$ mol/l) in aqueous solution at 37° C. The correlation between R1 or R2 as a function of the concentration is linear and the slope represents the relaxivity r1 (RUC) or r2 (R2/C) expressed as (1/second)×(1/mmol/l), i.e. $mM^{-1} \cdot s^{-1}$.

The compounds were prepared in different media: water, NaCl, citrate, phosphate, carbonate, cocktail of ions.

The Applicant has confirmed that the products obtained are stable and in particular do not undergo transmetallation by the appropriate protocols. Contrary to linear chelates in particular, in the presence of $ZnCl_2$, the product is completely stable (standard protocol: concentration of product=concentration of $ZnCl_2$=1.25 mM in the solution studied; temperature 37° C.).

EXAMPLE 1

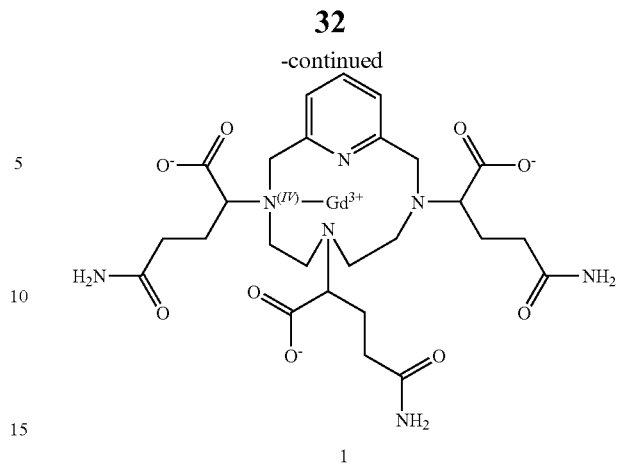

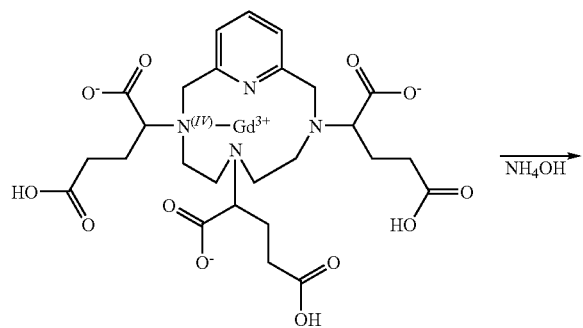

A solution comprising 1.05 mol of ammonia in 200 ml of water is prepared. The pH is adjusted to 6 with HCl. 17.5 g of gadolinium complex of 3,6,9,15-tetraazabicyclo[9.3.1]pentadeca-1(15),11,13-triene-3,6,9-tri(α-glutaric acid), 1.96 g of HOBT, 24.92 g of EDCI and 150 ml of dioxane are added to the preceding solution. The pH is adjusted to 6. After 24 h, the reaction medium is concentrated to approximately 70 ml. The reaction medium is precipitated from 700 ml of ethanol+200 ml of ether. The solid is filtered off and then purified by chromatography on silanized silica RP2, elution being carried out with water. 5.43 g of product 1 are obtained. m/z (ES+)=749.

EXAMPLE 2

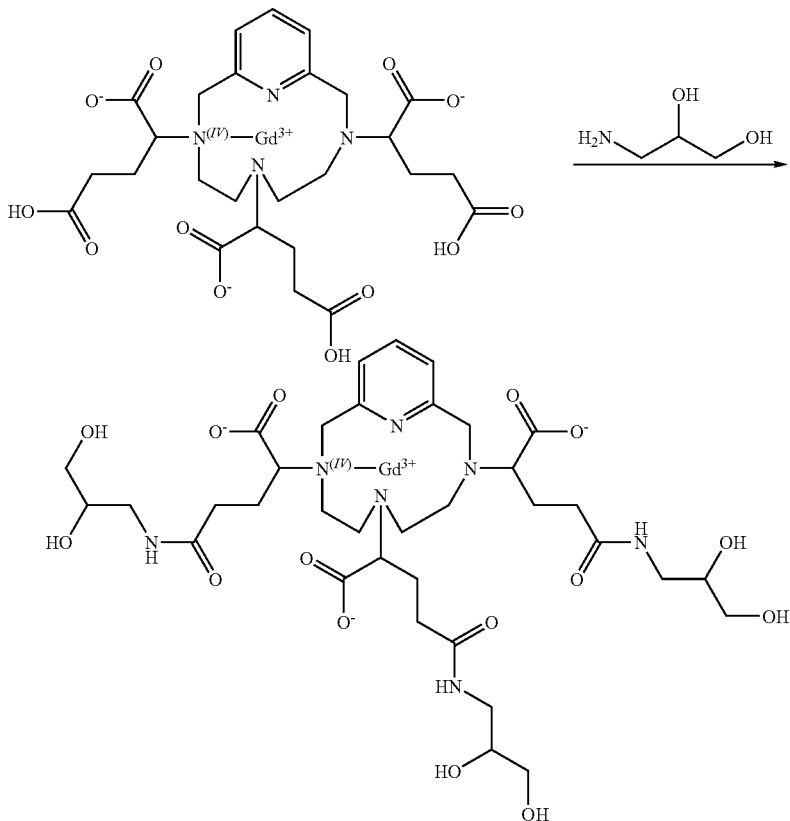

A solution comprising 0.763 g of 3-aminopropane-1,2-diol in 40 ml of water is prepared. The pH is adjusted to 6 with HCl. 2 g of gadolinium complex of 3,6,9,15-tetraazabicyclo[9.3.1]pentadeca-1(15),11,13-triene-3,6,9-tri(α-glutaric acid), 0.162 g of HOBT, 1.99 g of EDCI and 30 ml of dioxane are added to the preceding solution. The pH is adjusted to 6. After 24 h, the reaction medium is concentrated to approximately 20 ml. The reaction medium is precipitated from 100 ml of ethanol+100 ml of ether. The solid is filtered off and then purified by chromatography on RP18 silica, elution being carried out with water/CH₃CN: gradient from 100% to 90% (v/v). 980 mg of product 2 are obtained. m/z (ES+)=971.

EXAMPLE 3

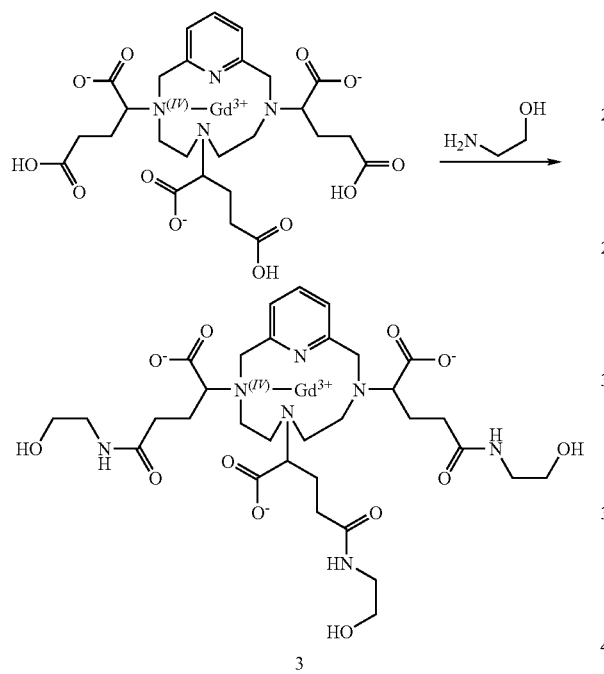

3

A solution comprising 0.512 g of ethanolamine in 40 ml of water is prepared. The pH is adjusted to 6 with HCl. 2 g of gadolinium complex of 3,6,9,15-tetraazabicyclo[9.3.1]pentadeca-1(15),11,13-triene-3,6,9-tri(α-glutaric acid), 0.162 g of HOBT, 1.99 g of EDCI and 30 ml of dioxane are added to the preceding solution.

The pH is adjusted to 6. After 24 h, the reaction medium is concentrated to approximately 20 ml. The reaction medium is precipitated from 100 ml of ethanol+100 ml of ether. The solid is filtered off and then purified by chromatography on RP18 silica, elution being carried out with water/CH₃CN: gradient from 100% to 90% (v/v). 560 mg of product 3 are obtained. m/z (ES+)=881.

HPLC: Lichrospher RP18 column, 250×4.6 mm, flow rate: 1 ml/min, UV detection at 201 nm.

Mobile phase: A: water/B: CH₃CN

| Time (min) | % A | % B |
|---|---|---|
| 0 | 98 | 2 |
| 20 | 70 | 30 |
| 30 | 50 | 50 | rt=10 to 11 min (several peaks)

EXAMPLE 4

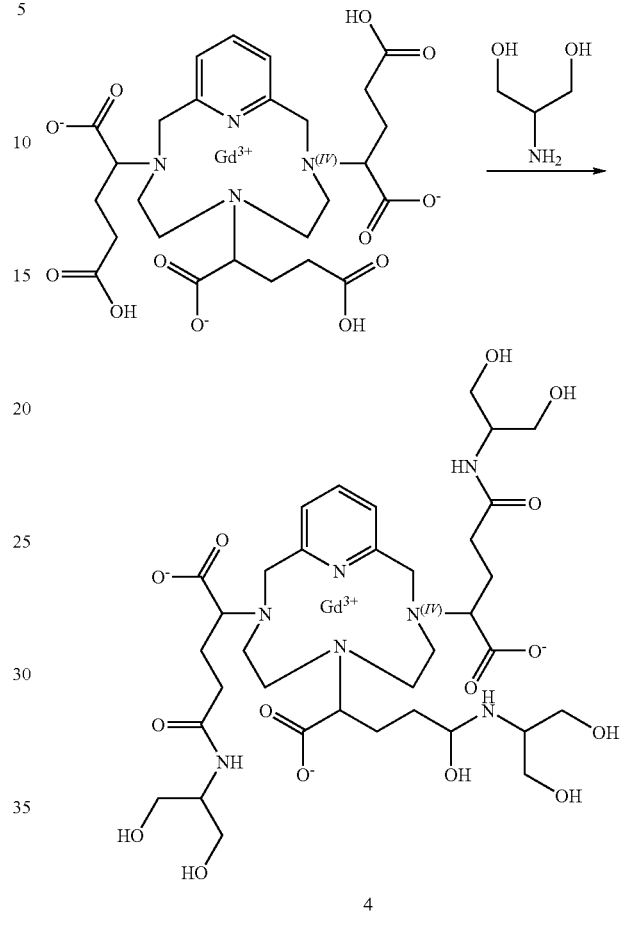

4

A solution comprising 6.1 g of serinol in 110 ml of water is prepared. The pH is adjusted to 6 with HCl. 11.25 g of gadolinium complex of 3,6,9,15-tetraazabicyclo[9.3.1]pentadeca-1(15),11,13-triene-3,6,9-tri(α-glutaric acid), 1.3 g of HOBT, 16 g of EDCI and 50 ml of dioxane are added to the preceding solution. The pH is adjusted to 6. After 24 h, the reaction medium is concentrated to dryness. The paste is hardened in ethanol. The solid is filtered off and then purified by chromatography on silanized silica RP2, elution being carried out with water. 5.2 g of product 4 are obtained. m/z (ES+)=971.

HPLC: Lichrospher RP18 column, 250×4.6 mm, flow rate: 1 ml/min, UV detection at 201 nm.

Mobile phase: A: water/B: CH₃CN

| Time (min) | % A | % B |
|---|---|---|
| 0 | 98 | 2 |
| 20 | 70 | 30 |
| 30 | 50 | 50 | rt=10 to 12 min (several peaks)

EXAMPLE 5

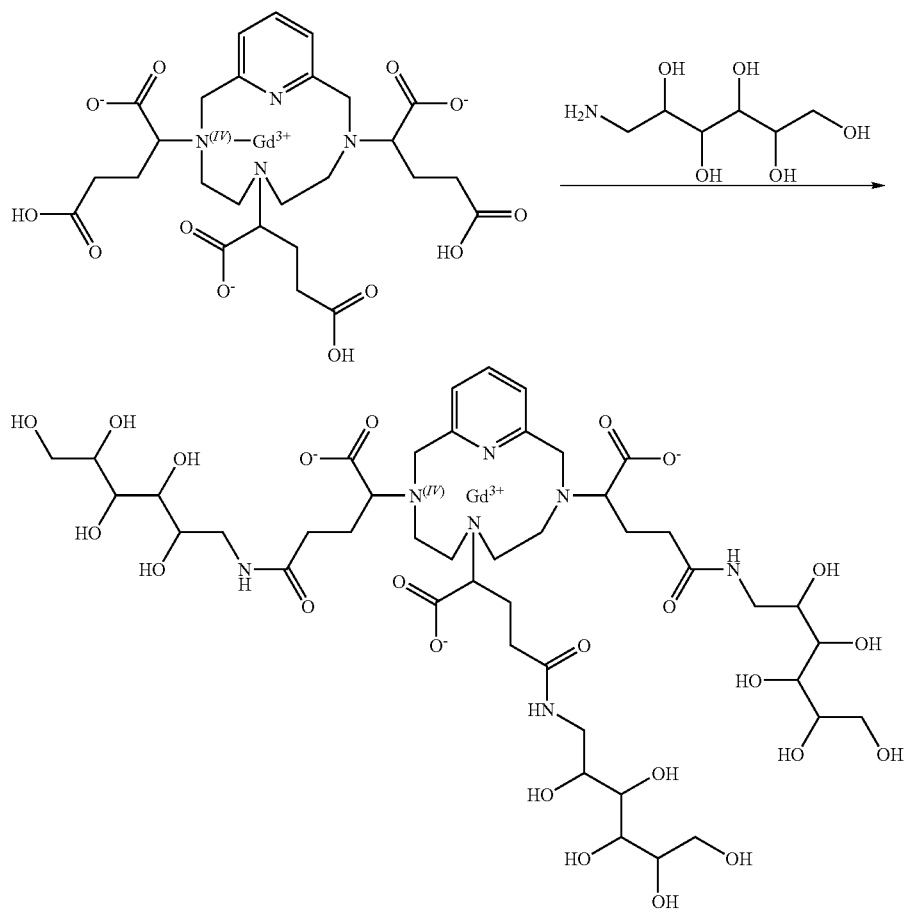

5

3.66 g of glucamine are dissolved in 70 ml of water. The pH is adjusted to 6 with HCl. 5 g of gadolinium complex of 3,6,9,15-tetraazabicyclo[9.3.1]pentadeca-1(15),11,13-triene-3,6,9-tri(α-glutaric acid), 0.372 g of HOBT, 4.576 g of EDCI and 50 ml of dioxane are added to the preceding solution. The pH is adjusted to 6. After reacting at AT for 9 h, 6 g of glucamine are added to the reaction medium and the pH is adjusted to 6 with HCl. 0.372 g of HOBT and 4.576 g of EDCI are added to the reaction medium. The pH is adjusted to 6. After reacting overnight, the reaction medium is concentrated. The 26 g of crude product are purified by preparative HPLC on a Lichrospher RP18 column. 4.7 g of product 5 are obtained. m/z (ES+)=

EXAMPLE 6

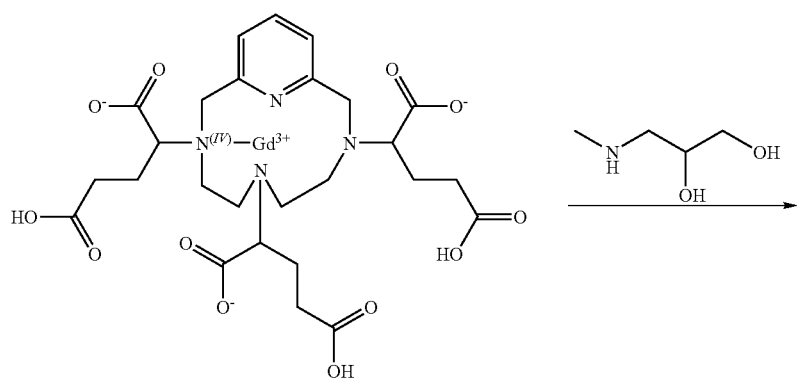

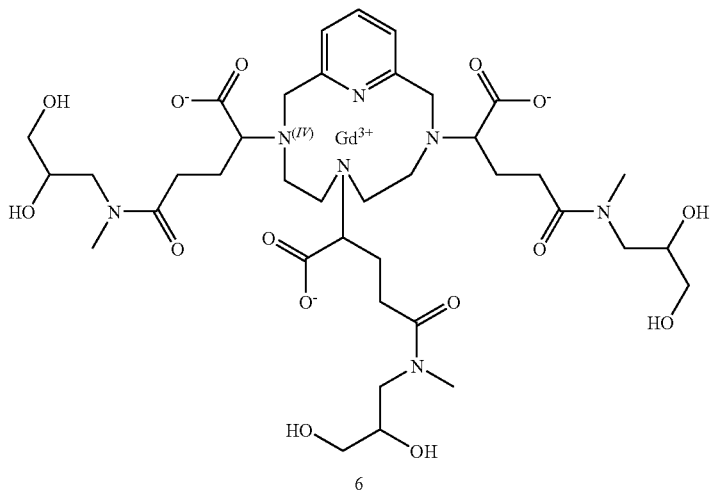

6

2.896 g of 3-methylamino-1,2-propanediol are dissolved in 100 ml of water. The pH is adjusted to 6 with HCl 5 g of gadolinium complex of 3,6,9,15-tetraazabicyclo[9.3.1]pentadeca-1(15),11,13-triene-3,6,9-tri(α-glutaric acid), 0.372 g of HOBT, 4.576 g of EDCI and 75 ml of dioxane are added to the preceding solution. The pH is adjusted to 6. After reacting at AT for 8 h, 2.896 g of 3-methylamino-1,2-propanediol are added to the reaction medium. The pH is adjusted to 6 with HCl. 0.372 g of HOBT and 4.576 g of EDCI are added to the reaction medium. The pH is adjusted to 6. After reacting overnight, the reaction medium is concentrated. The 29 g of crude product are purified by preparative HPLC on a Lichrospher RP18 column. 3.8 g of product 6 are obtained. m/z (ES+)=1213

EXAMPLE 7

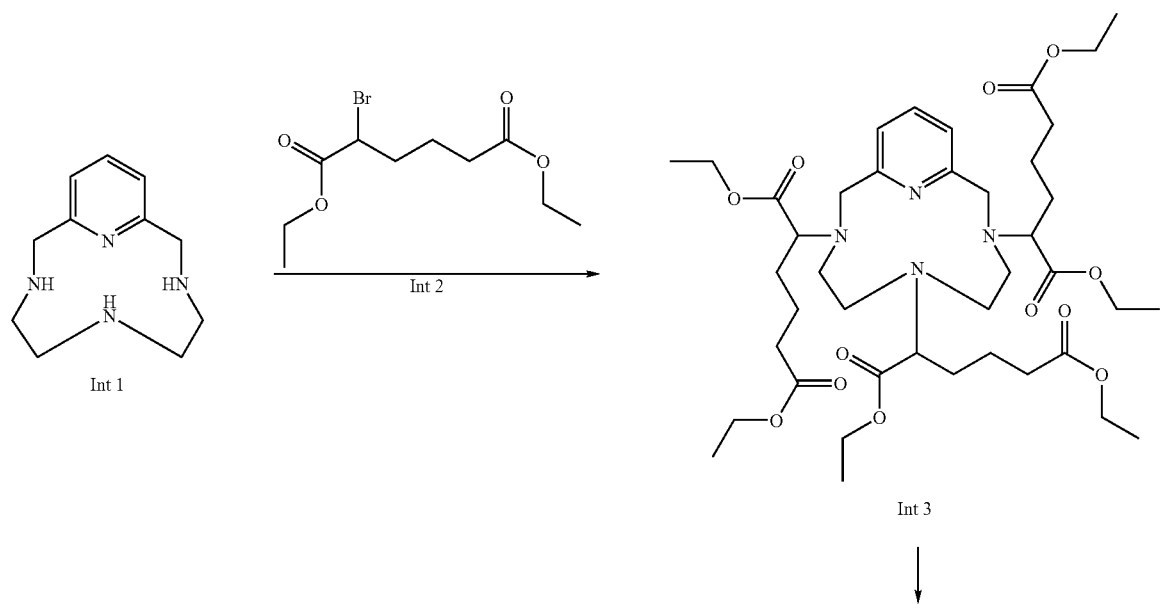

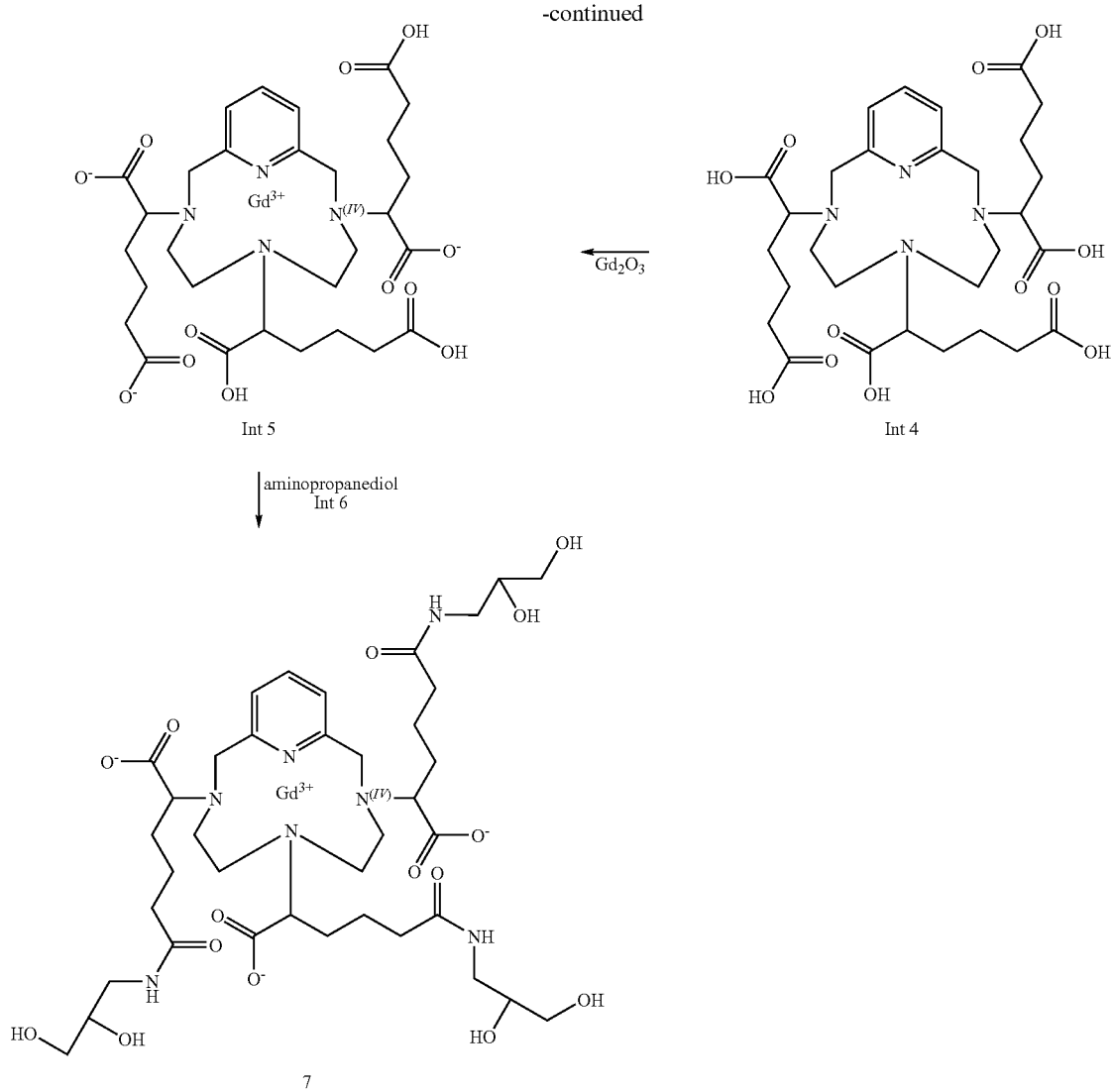

Intermediate 3:

g of compound Int. 1, 41 g of 2-bromohexanedioic acid diethylester (purity of 75%) and 16 g of $K_2CO_3$ are dissolved in 400 ml of acetonitrile. The solution is brought to reflux overnight. It is filtered and the filtrate is concentrated and then taken up in a water/HCl mixture at pH=2. The filtrate is washed with ether. The aqueous phase is neutralized and then extracted with $CH_2Cl_2$. The organic phase is concentrated. 12 g of intermediate 4 in the oil form are obtained. m/z=806

HPLC: Column: Symmetry, C18, 250×4.6 mm;
Mobile phase: A: water+TFA (pH=2.8)/B: $CH_3CN$

| Time | Flow rate | % A | % B |
|---|---|---|---|
| 0 | 1 | 98 | 2 |
| 5 | 1 | 90 | 10 |
| 8 | 1 | 90 | 10 |
| 13 | 1 | 85 | 15 |
| 25 | 1 | 60 | 40 |
| 30 | 1 | 40 | 60 |
| 45 | 1 | 20 | 80 | rt=34.5 min

Intermediate 4:

12 g of intermediate 3 are dissolved in 60 ml of 5N sodium hydroxide solution and 60 ml of methanol. The solution is brought to reflux overnight and is then concentrated. It is subsequently neutralized by passing through Amberlite IRC50 resin and then again concentrated. The oil obtained is hardened in ethanol. 9.5 g of intermediate 4 in the form of crystals are obtained with a yield of 100%. m/z=638

HPLC: Column: Symmetry, C18, 250×4.6 mm
Mobile phase: A: water+TFA (pH=2.8)/B: $CH_3CN$

| Time | Flow rate | % A | % B |
|---|---|---|---|
| 0 | 1 | 98 | 2 |
| 5 | 1 | 90 | 10 |
| 8 | 1 | 90 | 10 |
| 13 | 1 | 85 | 15 |
| 25 | 1 | 60 | 40 |
| 30 | 1 | 40 | 60 |
| 45 | 1 | 20 | 80 | rt=18 min (2 peaks)

Intermediate 5:

9.5 g of intermediate 4 are dissolved in 150 ml of water. The pH is adjusted to 6. 2.73 g of $Gd_2O_3$ are added to the solution, which is brought to 60° C. for 8 h. The solution is concentrated and then the residue is taken up in ethanol. 9 g of intermediate 5 in the form of white crystals are obtained. m/z=792.25

HPLC: Column: Symmetry, C18, 250×4.6 mm
Mobile phase: A: water+TFA (pH=2.8)/B: $CH_3CN$

| Time | Flow rate | % A | % B |
|---|---|---|---|
| 0 | 1 | 98 | 2 |
| 5 | 1 | 90 | 10 |
| 8 | 1 | 90 | 10 |
| 13 | 1 | 85 | 15 |
| 25 | 1 | 60 | 40 |
| 30 | 1 | 40 | 60 |
| 45 | 1 | 20 | 80 | rt=18.3 to 21 min (4 peaks)

Product 7:

5 g of 3-aminopropane-1,2-diol are dissolved in 120 ml of water and the pH is adjusted to 6.9 g of intermediate 5, 1.04 g of HOBT and 12.8 g of EDCI are added to the preceding solution. The solution is stirred at pH 6 for 18 h. The solution is evaporated, the oil obtained is taken up in ethanol and the crystals which were formed are filtered off. The crystals obtained are purified by chromatography on silanized silica RP2. 2.9 g of product 7 are obtained. m/z=1012.19

HPLC: Column: Symmetry, C18, 250×4.6 mm
Mobile phase: A: water+TFA (pH=2.8)/B: $CH_3CN$

| Time | Flow rate | % A | % B |
|---|---|---|---|
| 0 | 1 | 98 | 2 |
| 5 | 1 | 90 | 10 |
| 8 | 1 | 90 | 10 |
| 13 | 1 | 85 | 15 |
| 25 | 1 | 60 | 40 |
| 30 | 1 | 40 | 60 |
| 45 | 1 | 20 | 80 | rt=13 min (3 peaks)

COMPARATIVE EXAMPLES 8 AND 9

Products of the Prior Art (U.S. Pat. No. 5,403,572)

The Applicant has had to prepare appropriate protocols.

COMPARATIVE EXAMPLE 8

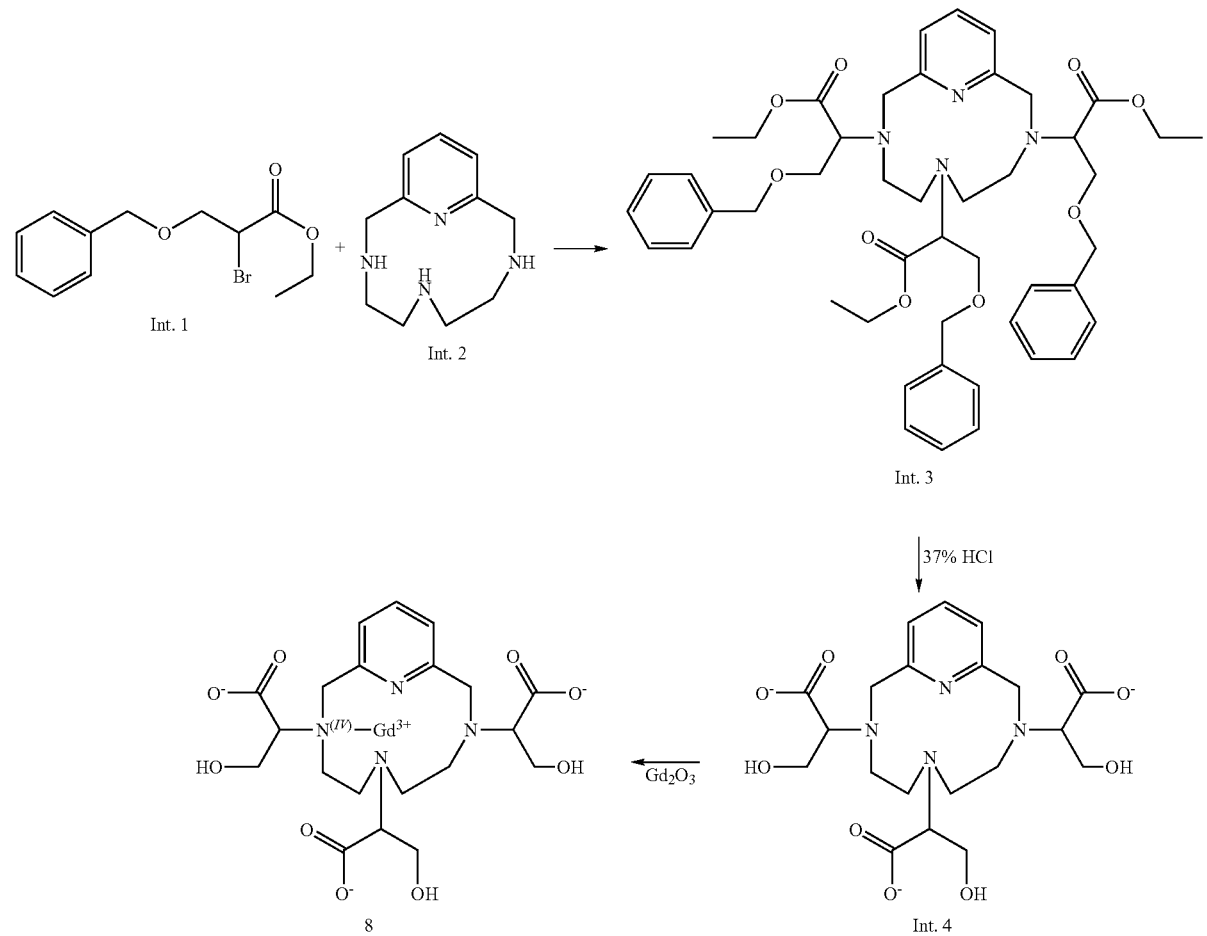

Int. 3:

3.83 g of compound Int. 1 and 12.82 g of anhydrous calcined $K_2CO_3$ are introduced into 50 ml of acetonitrile. After stirring at reflux for 30 min, 15 g of ethyl 3-benzyloxy-2-bromopropanoate are added. After reacting at reflux with stirring for 2 h 15, the suspension, still hot, is filtered through a sintered glass funnel. The solid is washed with acetonitrile. The filtrates are concentrated and then taken up in 150 ml of 5N HCl. The aqueous solution is extracted three times with $Et_2O$, then three times with ethyl acetate and then three times with dichloromethane. The organic phases resulting from the extractions with dichloromethane are combined, dried over $MgSO_4$ and then concentrated. 6.4 g of product Int. 3 are obtained with a yield of 67%. m/z (ES+)=826.

Int. 4:

Int. 3 is dissolved in 200 ml of 37% HCl and then left to react with stirring at 40° C. for 9 days. The reaction medium is concentrated and then purified by chromatography on silanized silica RP2 (elution with water). 2.9 g of product Int. 4 are obtained with a yield of 80%.

m/z (ES+)=468.

Product 8:

Int. 4 is dissolved in 120 ml of water. The pH is adjusted to 5 and then 1.134 g of $Gd_2O_3$ are added. After reacting with stirring at 40° C. for 6 h while maintaining the pH between 5.2 and 5.7 with 1N HCl, the reaction medium is filtered through a 0.22 μm filter, concentrated and then purified by chromatography on silanized silica RP2 (elution with water). 1.4 g of product 8 are obtained with a yield of 36%. m/z (ES+)=625.

COMPARATIVE EXAMPLE 9

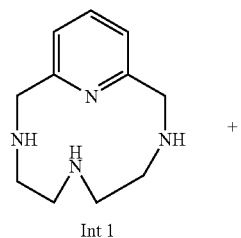

Int 1

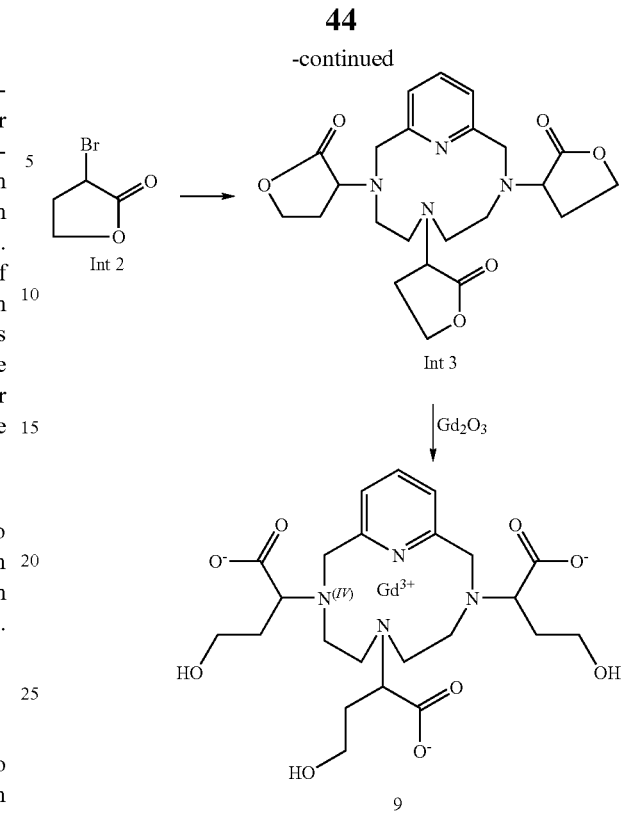

Int. 3:

10 g of PCTA and 39.4 g of anhydrous calcined $K_2CO_3$ are dissolved in 100 ml of acetonitrile at reflux under argon. 26.07 g of α-bromo-γ-butyrolactone are added. After reacting at reflux with very vigorous stirring and under argon for 24 h, the reaction medium is filtered. The solid is washed with acetonitrile. The liquors are concentrated. 5.8 g of product are obtained and then purified on 200 g of silica, elution being carried out with $CH_2Cl_2$/MeOH (9/1). 1.93 g of product, Int. 3 are obtained with a yield of 13%.

m/z (ES+)=668

Product 9:

The Int. 3 is dissolved in 50 ml of water. The pH is adjusted to 5 and the temperature to 60° C. 0.762 g of $Gd_2O_3$ are added to the reaction medium. The pH is maintained between 5 and 5.5 during the 5 hours of reaction at 80° C. The reaction medium is filtered through a 0.22 μm filter and then concentrated. 2.71 g of product are obtained and then purified by chromatography on silanized silica. 1.38 g of product 9 are obtained with a yield of 50%.

EXAMPLE 10

The complex according to Example 2

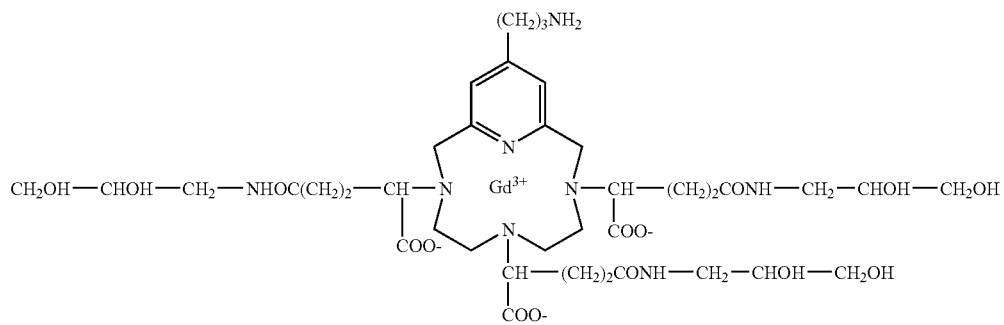

is coupled to a biovector comprising a carboxylic acid functional group or indirectly using a bonding group.

For example, a peptide biovector, the characteristics of which are collated in Table 3 below, is coupled using a squarate bonding group.

| No. | Sequence | MW | w in mg |
|---|---|---|---|
| 1 | Asp(tBu)-Ala-His(Trt)-Ser(tBu)-Phe-Ser(tBu)OH | 1073.31 | 172 |
| 2 | Leu-Ile-Lys(Boc)-Lys(Boc)-Pro-Phe-OH | 945.22 | 151 |
| 3 | Pro-Gly-Asp-(tBu)-Leu-Ser(tBu)-Arg(Pbf)-OH | 1008.25 | 161 |

Stage 1: Formation of the Compound precipitated from 120 ml of ether. The yellowish oil is washed with ethyl ether. The solid obtained is filtered off and then washed with dichloromethane.

After filtration, 700 mg of a white solid are obtained.

State 2: Coupling of the Peptides No. 1, 2 or 3 with the Squarate Derivative

The compound obtained in stage 1 (155.5 mg, $1.35 \times 10^{-4}$ mol) is dissolved in 15 ml of aqueous $Na_2CO_3$ solution, pH 9.4. The protected peptide 1, 2 or 3 ($1.6 \times 10^{-4}$ mol) is introduced while maintaining the pH at 9.4 by addition of $Na_2CO_3$.

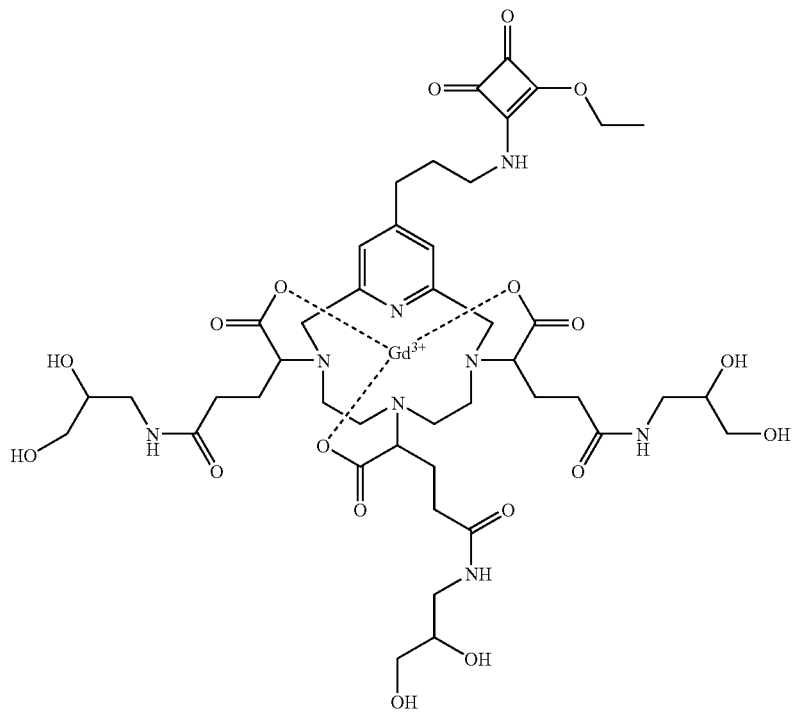

1 g of compound according to Example 2

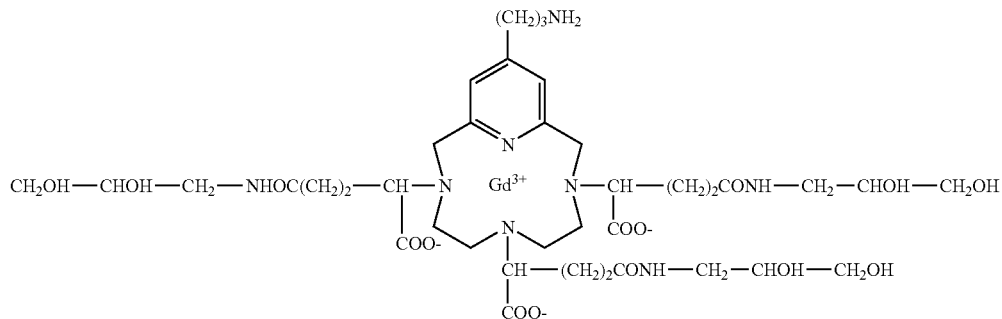

is dried with toluene and then suspended in 20 ml of anhydrous DMSO under an argon blanket. 0.4 ml of $Et_3N$ dried over sieves (1.7 eq) and 720 mg of diethyl squarate (Aldrich, 2.5 eq.) are then added. The mixture is stirred at ambient temperature under an argon blanket for 1 hour. The medium is If the peptide is not soluble in water, a few drops of DMF are added until dissolution is complete.

After reacting at ambient temperature for 48 h, the medium is precipitated from an ethanol/ethyl ether mixture. The precipitate is filtered off and then dried.

Stage 3: Deprotection

The compound obtained in stage 2 is dissolved in a mixture of 10 cm$^3$ of TFA/TIS/H$_2$O in the proportions 90/5/5. The medium is stirred at ambient temperature for 5 h and then the solvent is evaporated under reduced pressure. The residue is taken up in ethyl ether and the precipitate is filtered off and then dried. The product is subsequently purified by preparative HPLC on a Symmetry® column with an eluent composed of water/TFA pH 3/CH$_3$CN.

Specific coupled compounds, for example the compounds 10a, 10b and 10c, which follow, functionalized in the C position, are obtained.

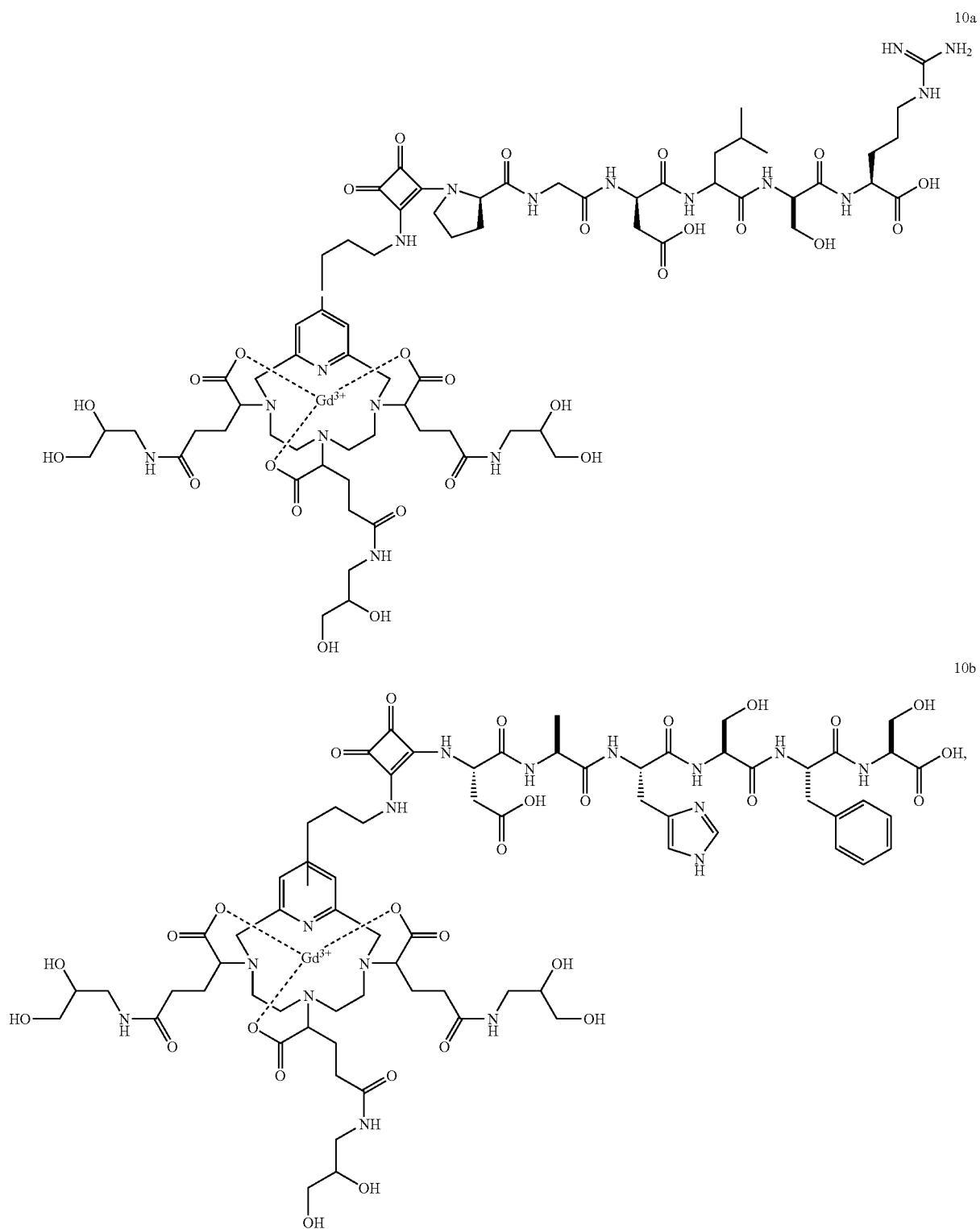

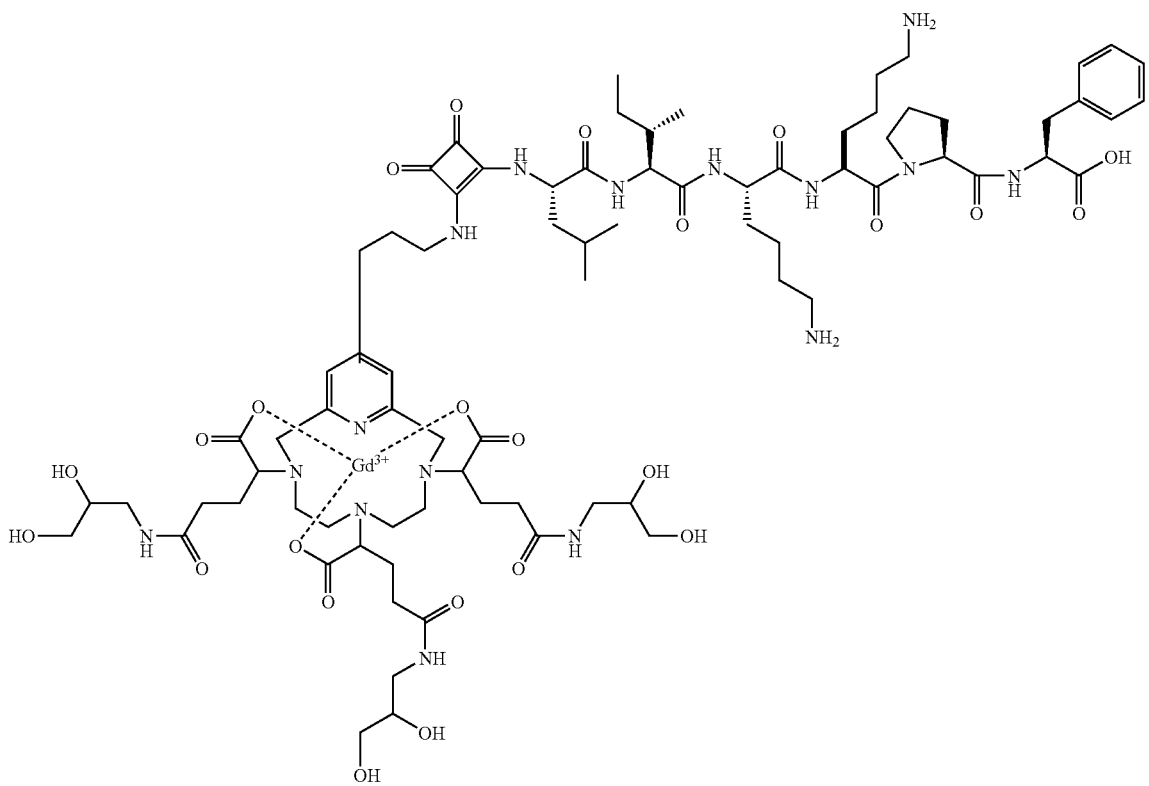
It is also possible to graft biovectors to the aminoalcohol branches in the N-functionalized PCTA position of the PCTA ring by selective coupling with a nitrogen atom of the ring.
EXAMPLE 11
Compound Possessing a DO3A Backbone
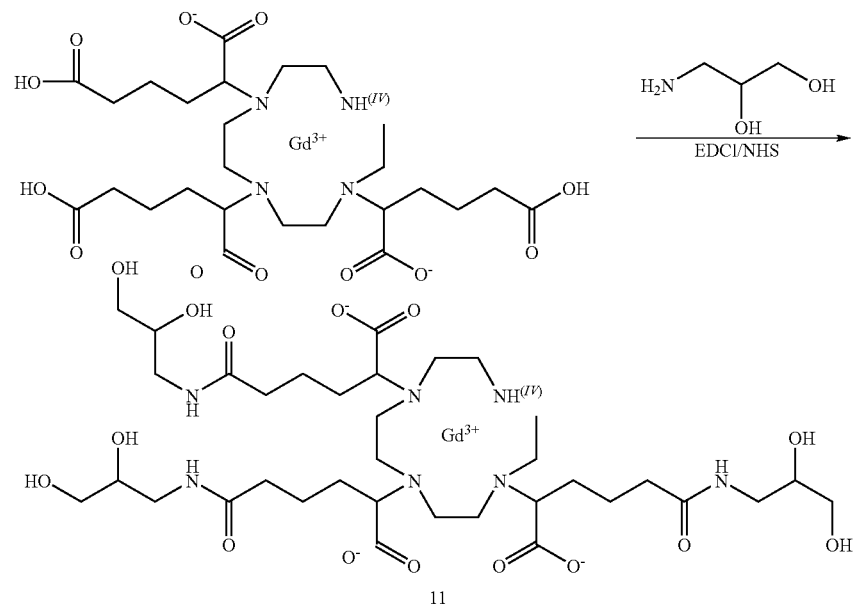

A solution comprising 2.6 g of 3-aminopropane-1,2-diol in 60 ml of water is prepared. The pH is adjusted to 6 with HCl. 6 g of gadolinium complex of 2-[4,7-bis(1,4-dicarboxybutyl)-1,4,7,10-tetraazacyclododec-1-yl]hexanoic acid are added to the preceding solution. The pH is again adjusted before adding 0.71 g of sulpho-NHS and 0.62 g of EDCI. The pH is monitored and adjusted to 6 with 2N NaOH. After one night at AT, the reaction medium is concentrated to approximately 20 ml and then precipitated from 100 ml of ethanol. The solid is filtered off, washed with ethanol and diethyl ether and then purified on silanized silica RP2 with elution solely with water. 2.2 g of product 11 are obtained. m/z (ES+)=979

HPLC: Column: Lichrospher RP18, 5 μm, 100 Å, 250×4.6 mm, flow rate: 1 ml/min. UV detection at 201 nm. Mobile phase: A: water (TFA pH 2.8)/CH$_3$CN

| Time (min) | % A | % B |
|---|---|---|
| 0 | 98 | 2 |
| 20 | 70 | 30 |
| 22 | 98 | 2 |
| 30 | 98 | 2 | rt=7.8 min (2 peaks)

EXAMPLES 12 TO 19

The Applicant has, according to analogous syntheses, prepared in particular the following compounds.

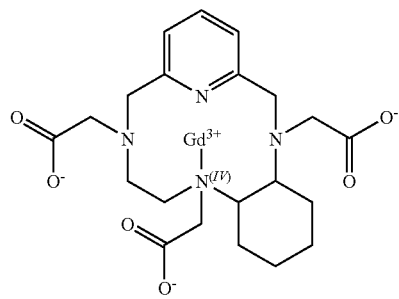

12

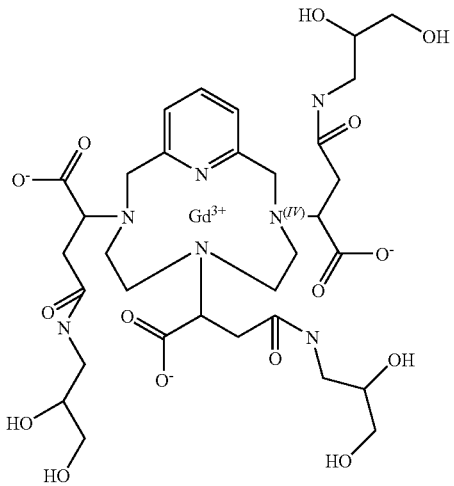

13

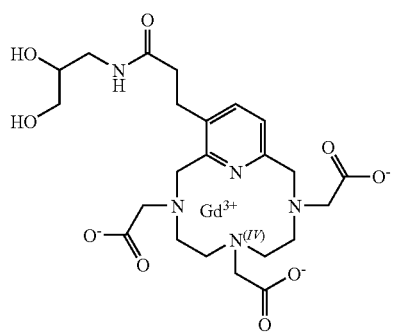

14

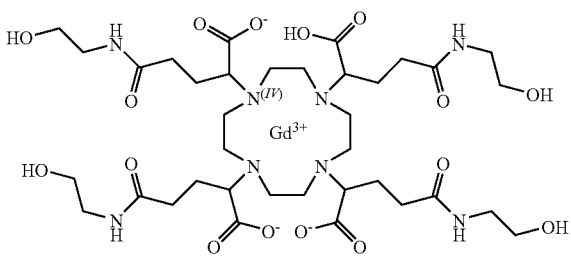

15

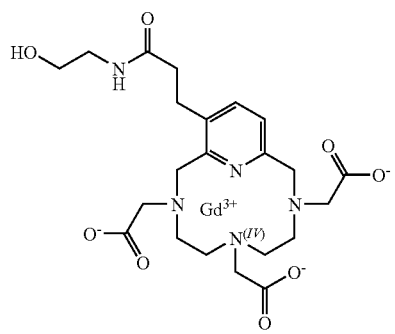

16

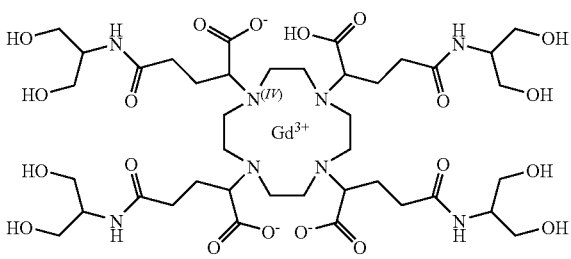

17

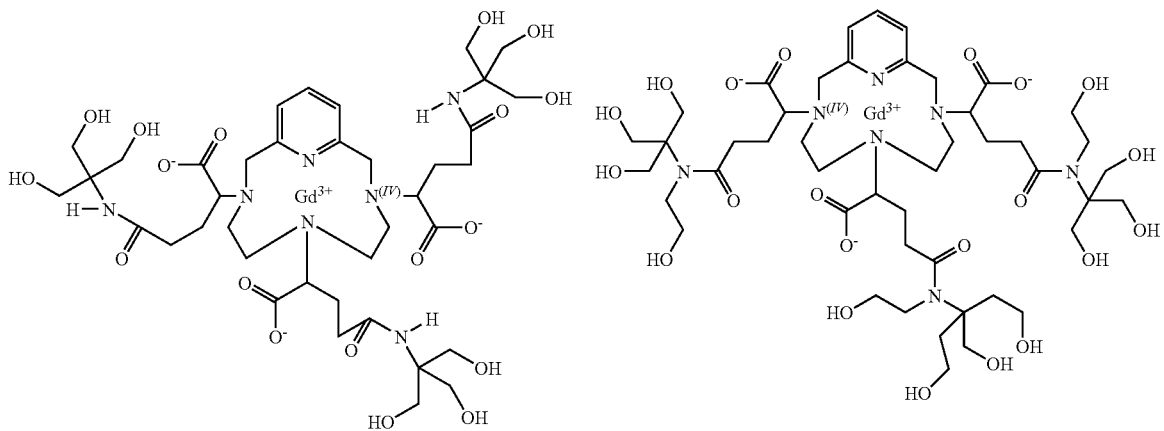

EXAMPLE 20

In Vivo Imaging Studies

Very advantageous results have been obtained notably for the detection of glioma. Compounds II (example 2) was compared to Dotarem® ans MultiHance(® for the detection of C6 glioma in rat (n=6/product). Each animal received all the three products at the same dose (0.1 mmol/kg) in a random order. A minimal delay of 4 hours has been respected between the injections in order to avoid remaining contrast from the previous injection. Enhancement was follow-up during 30 min with a T1w-Spin Echo sequence (TR/TE=498/14.2 ms, FOV=4×4 cm2, slice thickness 2 mm, interslice distance 3 mm, 192×192 matrix, 2 accumulation) on a 2.35 T system (BioSpec 24/40, Bruker, Germany). Enhancement of the lesions have been quantitatively (ROIs) and qualitatively (blinded cotation) evaluated. All the lesions have been depicted with all the contrast agents. However among the three contrast agents, compound II induced a 2 fold-more pronounced contrast between the lesion and the healthy brain. The blinded reader judged the contrast between tumor and healthy brain to be distinctively higher for all the rats injected with compound II.

The invention claimed is:

1. A compound having formula (IIa):

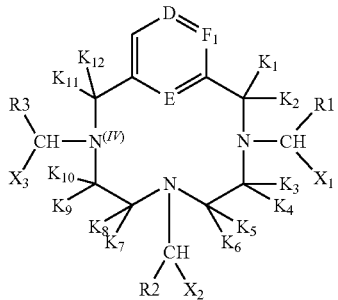

in which:

R1, R2 and R3 represent, independently of one another, —COOH, —P(O)(OH)$_2$ or —R$_6$—P(O)—OH in which R$_6$ represents an H atom or a C$_1$-C$_3$ alkyl group;

$X_1$, $X_2$ and $X_3$ represent, independently of one another, L-Y in which L represents a C$_1$-C$_3$ alkyl group, Y represents —CONH$_2$, —CO—NR7R8 or —NR7-CO—R8, in which R7 represents H, a C$_1$-C$_6$ alkyl group or a C$_1$-C$_6$ hydroxyalkyl group, and R8 represents a C$_1$-C$_6$ alkyl or C$_1$-C$_6$ hydroxyalkyl group, provided that at least R7 or R8 represents a C$_1$-C$_6$ hydroxyalkyl group;

D represents CH or N;

E represents CH or N;

$F_1$ represents CH or N;

$K_1$ to $K_{12}$ each independently represent H, —(CH$_2$)$_j$—CH$_3$ or —(CH$_2$)$_i$—OH, in which j=0 to 3 and i=1 to 3, or $K_3$ or $K_4$ with $K_5$ or $K_6$, and/or $K_7$ or $K_8$ with $K_9$ or $K_{10}$ form a ring having 3 to 6 carbon atoms;

or an isomer, an enantiomer or a diastereoisomer of these or their mixtures.

2. Compound according to claim 1 of formula (IIa), wherein E represents an N atom and D and $F_1$ represent CH.

3. Compound according to claim 1 of formula (IIa), wherein $X_1$, $X_2$ and $X_3$ independently represent —(CH$_2$)$_n$—CO—NR7R8 or —(CH$_2$)$_n$—NR7-CO—R8, in which n is between 1 and 3, R7 represents H or a methyl group and R8 represents a C$_1$-C$_6$ hydroxyalkyl group.

4. Compound according to claim 3 of formulae (IIa)

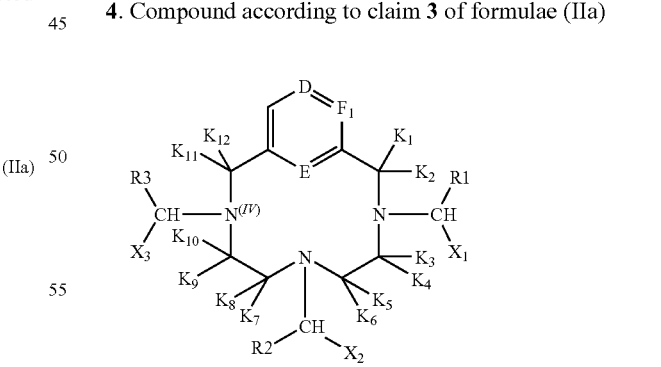

wherein $X_1$, $X_2$ and $X_3$ independently represent —(CH$_2$)$_n$—CONR7R8 or —(CH$_2$)$_n$—NR7-CO—R8, in which n is between 1 and 3, R7 represents H or a methyl group and R8 represents a C$_1$-C$_4$ hydroxyalkyl group.

5. Compound according to claim 4, wherein $X_1$, $X_2$ and $X_3$ independently represent —(CH$_2$)$_n$—CONR7R8, in which n is between 1 and 3, R7 represents H and R8 represents —CH$_2$—CH$_2$OH, —CHOH—CH$_2$OH, —CH—(CH$_2$OH)$_2$, —CH$_2$—(CHOH)$_p$—CH$_2$OH, with p=1 to 4, or —C—(CH$_2$OH)$_3$.

6. Multimer of a compound according to claim 1.

7. Complex of a compound according to claim 1 with M, M representing an ion of a paramagnetic metal of atomic number 21-29, 42-44 or 58-70 or a radionuclide chosen from $^{99}$Tc, $^{117}$Sn, $^{111}$In, $^{97}$Ru, $^{67}$Ga, $^{68}$Ga, $^{89}$Zr, $^{177}$Lu, $^{47}$Sc, $^{105}$Rh, $^{188}$Re, $^{60}$Cu, $^{62}$Cu, $^{64}$Cu, $^{67}$Cu, $^{90}$Y, $^{159}$Gd, $^{149}$Pr and $^{166}$Ho.

8. Complex of a multimer according to claim 6 with M, M representing an ion of a paramagnetic metal of atomic number 21-29, 42-44 or 58-70 or a radionuclide chosen from $^{99}$Tc, $^{117}$Sn, $^{111}$In, $^{97}$Ru, $^{67}$Ga, $^{68}$Ga, $^{89}$Zr, $^{177}$Lu, $^{47}$Sc, $^{105}$Rh, $^{188}$Re, $^{60}$Cu, $^{62}$Cu, $^{64}$Cu, $^{67}$Cu, $^{90}$Y, $^{159}$Gd, $^{149}$Pr and $^{166}$Ho.

9. Complex according to claim 7 or 8, wherein the ion of a paramagnetic metal is chosen from Gd$^{3+}$, Mn$^{2+}$ and Fe$^{3+}$.

10. Complex according to claim 7 or 8, wherein it exhibits:
- a relaxivity in water of at least 10 mM$^{-1}$s$^{-1}$Gd$^{-1}$,
- an osmolality of between 800 and 1200 mOsm/kg, for a Gd concentration of 400 to 600 mM, and
- a substantially stable relaxivity between 20 and 300 MHz, or an increase in relaxivity beyond 20 MHz.

11. Complex according to claim 7 or 8, wherein it is chosen from the complexes of following formulae:

2

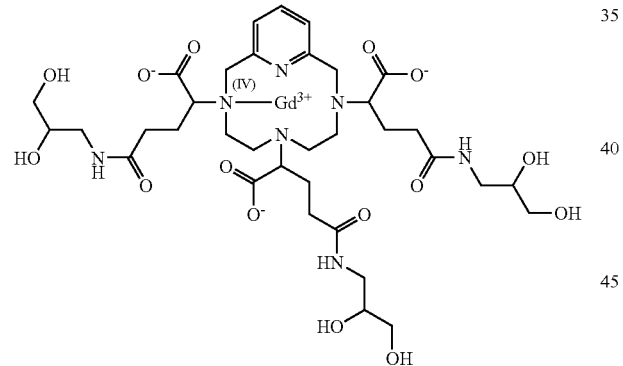

3

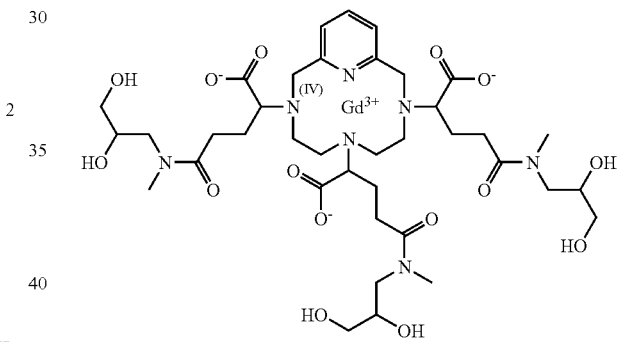

4

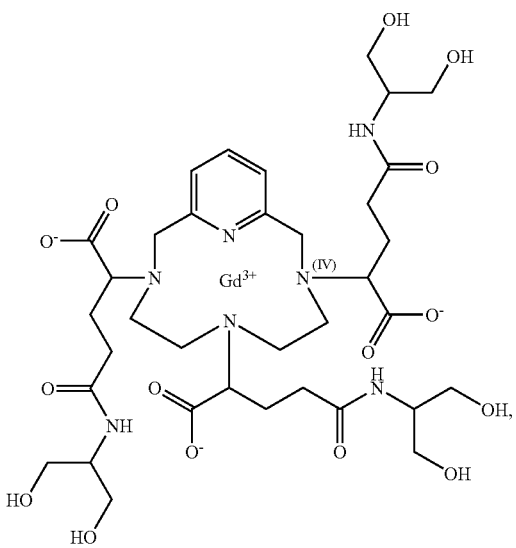

6

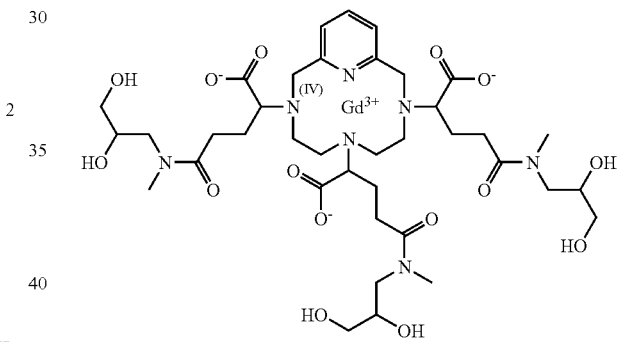

18

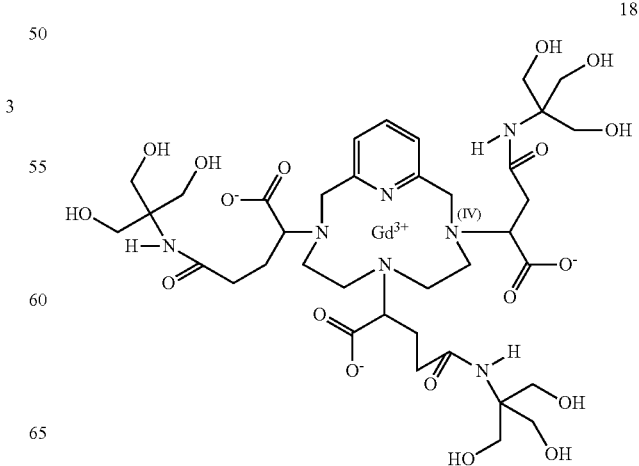

-continued
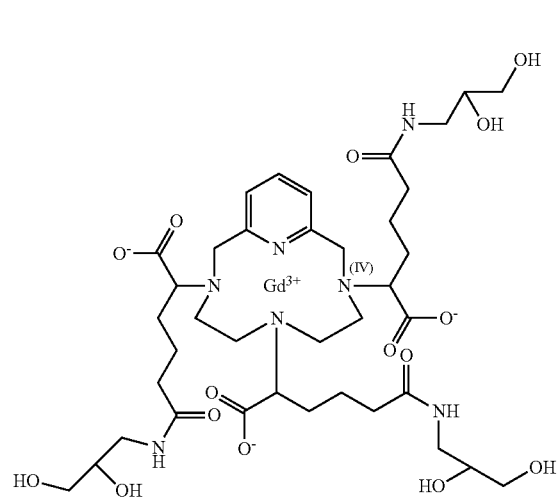
7
-continued
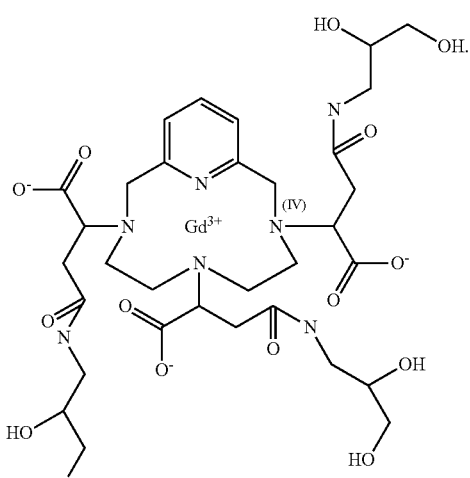
13
12. Complex according to claim 7 or 8, wherein it is chosen from the complexes of following formulae:
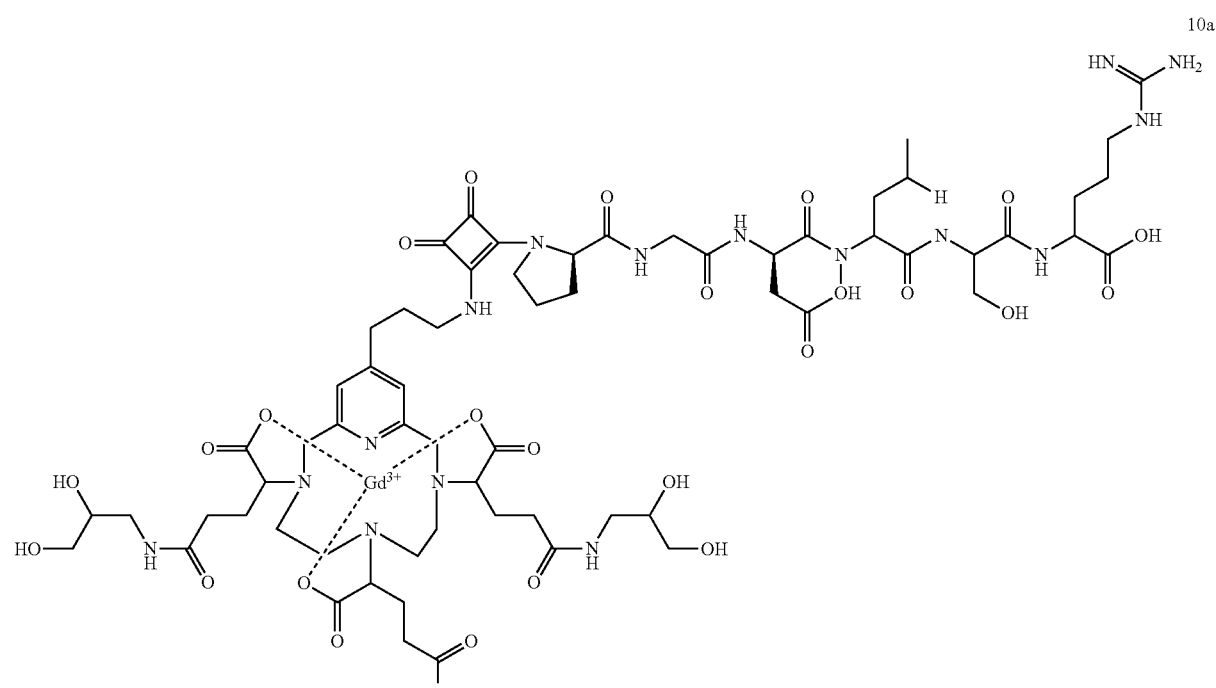
10a
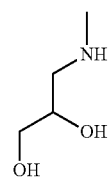

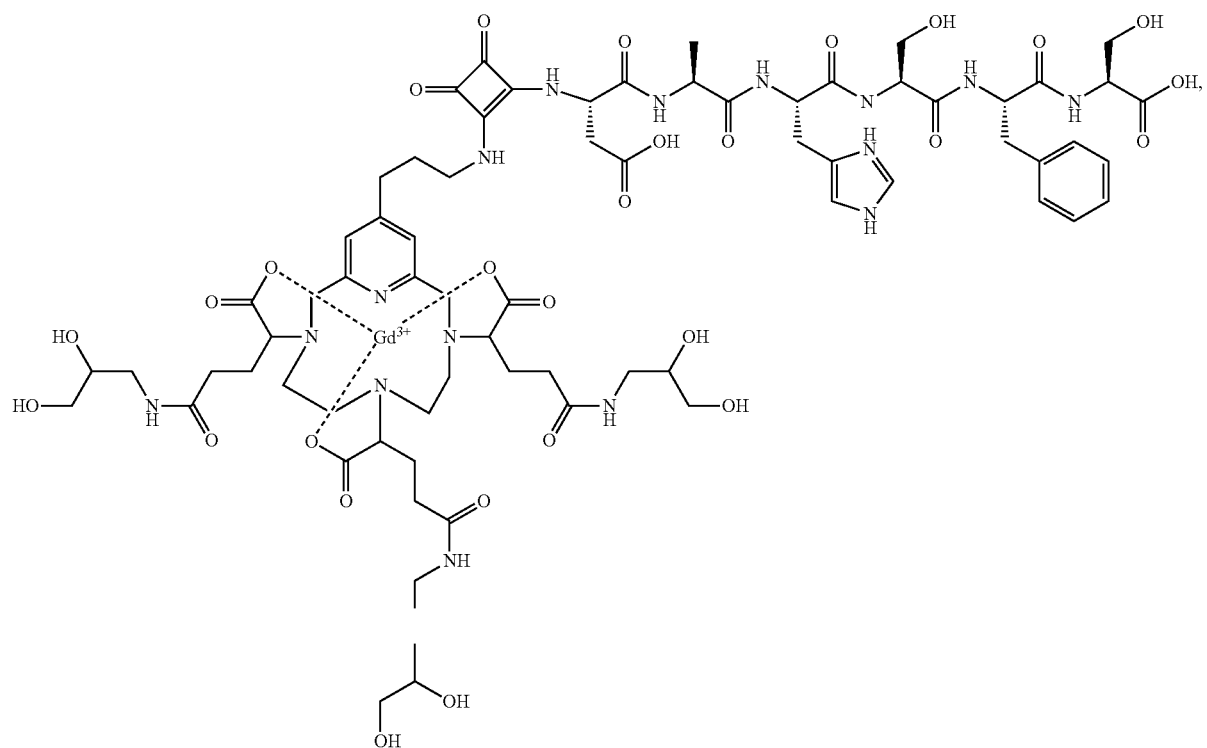
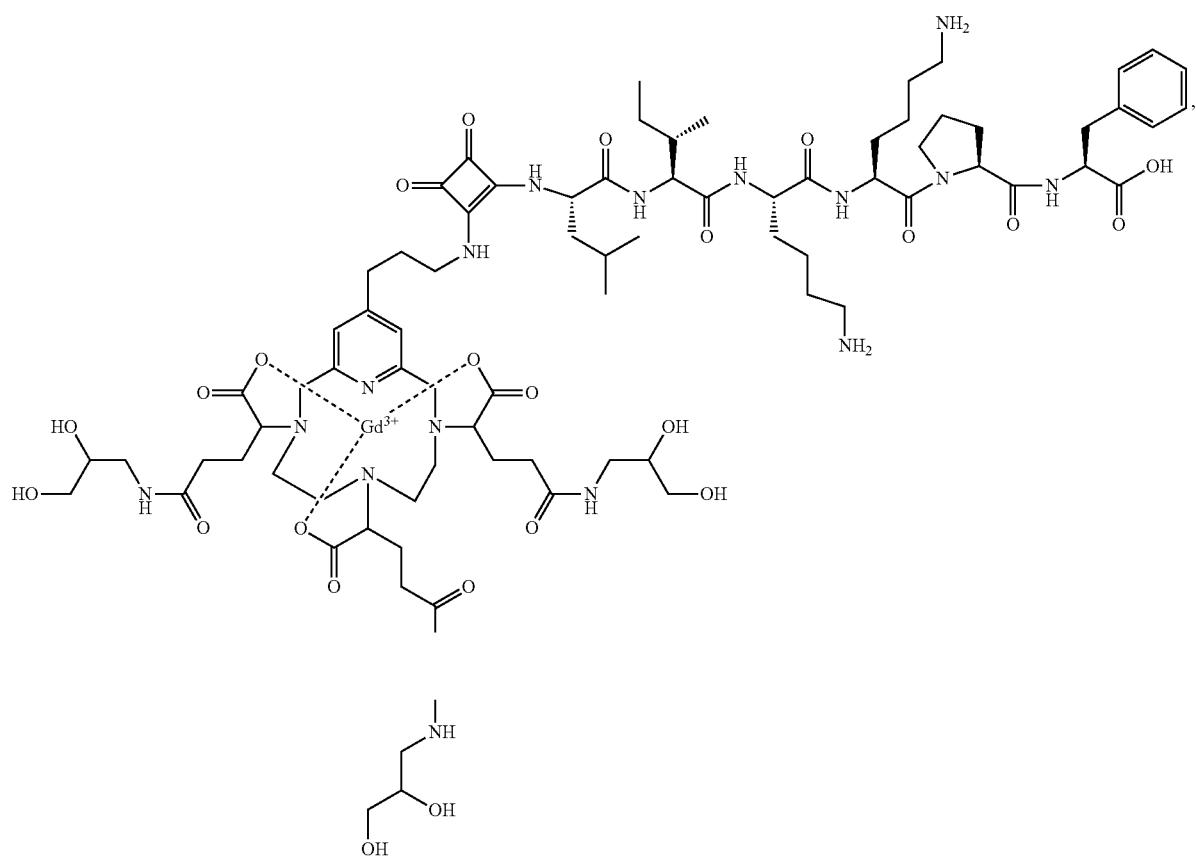

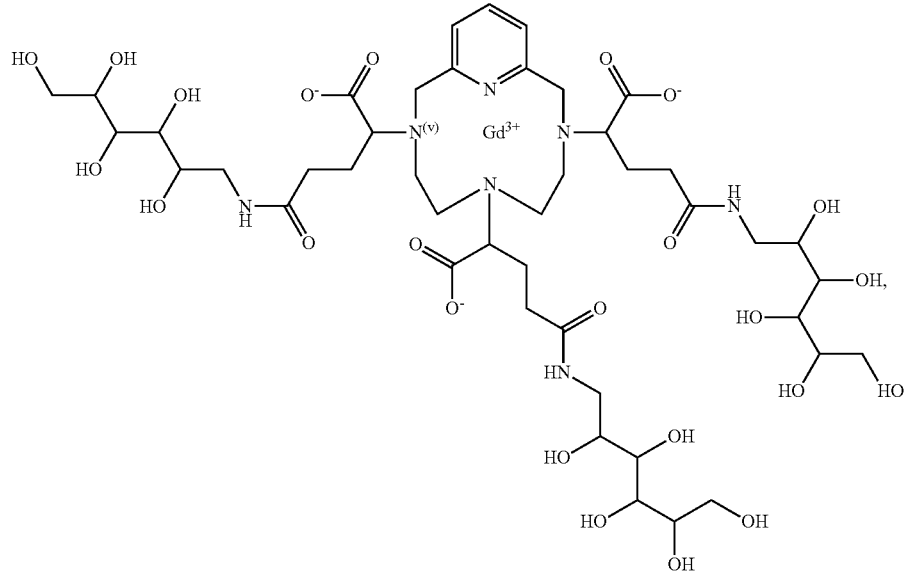

5

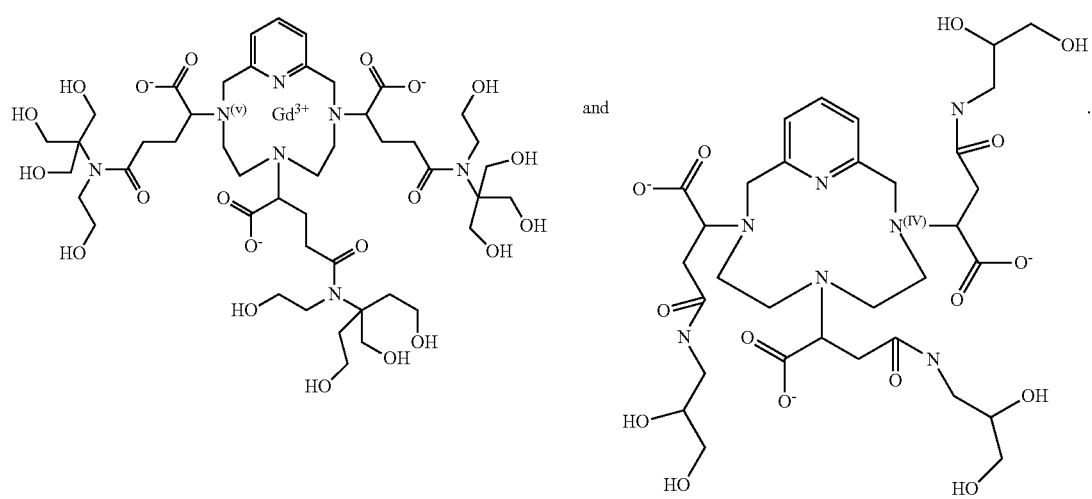

19 and 13

13. Pharmaceutical composition comprising a compound according to claim 1 or a multimer according to claim 6 or a complex according to claim 7 or 8, a pharmaceutically acceptable vehicle and optionally formulation additives.

14. Lipid pharmaceutical composition comprising a compound according claim 1 or a multimer according to claim 6 or a complex according to claim 7 or 8, bonded to a lipid nanoparticle.

15. Diagnostic composition for magnetic resonance imaging, comprising a compound according to claim 1 or a multimer according to claim 6 compound according to claim 9 or a complex according to claim 7 or 8.

16. Process for the preparation of a metal complex according to claim 7 of a compound of formula (IIa) in which $X_1$, $X_2$ and $X_3$ independently represent —$(CH_2)_n$—CO—NR7R8, in which n=1 to 3 and R7 and R8 are as defined in claim 1, comprising the stages:

a) reacting the condensed macrocycle of following formula (IV)

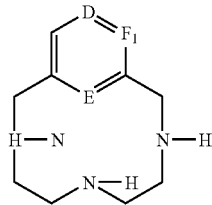

IV in which D, E and F$_1$ are as defined in claim 1, with a compound of formula R'OOC—CHQ-(CH$_2$)$_n$—COOR', in which n=1 to 3, Q represents a leaving group, and R' represents H or a (C$_1$-C$_3$)alkyl or benzyl group, in order to obtain the hexaacid or ester of following formula (V)

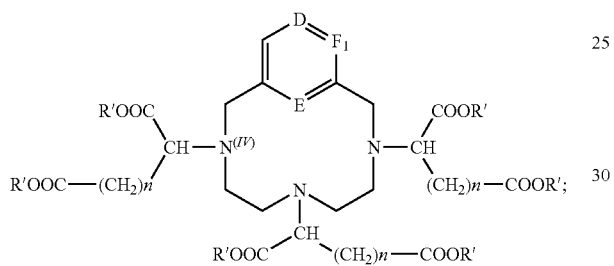

V b) optionally hydrolysing or hydrogenating the ester functional groups of the hexaacid of formula (V) when R' is other than H, in order to obtain the hexaacid of formula (Va)

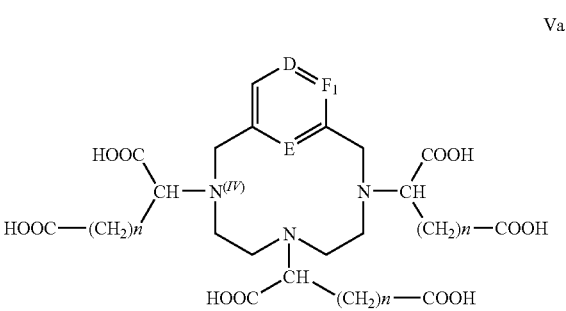

Va in which D, E and F$_1$ are as defined above and n is between 1 and 3;

c) reacting the hexaacid of formula (Va) with a salt or an oxide of the metal to be complexed, in order to obtain the corresponding complex or one of its salts with a base;

d) reacting the complex, in the presence of an agent which activates carboxylic acid functional groups, with the aminoalcohol group or groups NHR7R8, in which R7 and R8 are as defined in claim 1, in order to obtain the triamide of formula (IIa), in which X$_1$, X$_2$ and X$_3$ independently represent —(CH$_2$)$_n$—CO—NR7R8 in which n=1 to 3 and R7 and R8 are as defined in claim 1.

\* \* \* \* \*